United States Patent
Mahapatra et al.

(10) Patent No.: US 11,937,872 B2
(45) Date of Patent: *Mar. 26, 2024

(54) EPICARDIAL ABLATION CATHETER AND METHOD OF USE

(71) Applicant: University of Virginia Patent Foundation, Charlottesville, VA (US)

(72) Inventors: Srijoy Mahapatra, Edina, MN (US); George T. Gillies, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 341 days.

This patent is subject to a terminal disclaimer.

(21) Appl. No.: 16/236,664

(22) Filed: Dec. 31, 2018

(65) Prior Publication Data
US 2019/0274757 A1 Sep. 12, 2019

Related U.S. Application Data

(63) Continuation of application No. 12/530,938, filed as application No. PCT/US2008/056816 on Mar. 13, 2008, now Pat. No. 10,166,066.
(Continued)

(51) Int. Cl.
*A61B 18/14* (2006.01)
*A61B 18/00* (2006.01)

(52) U.S. Cl.
CPC . *A61B 18/1492* (2013.01); *A61B 2018/00011* (2013.01); *A61B 2018/00029* (2013.01);
(Continued)

(58) Field of Classification Search
CPC ...... A61B 18/1492; A61B 2018/00011; A61B 2018/00029; A61B 2018/00035;
(Continued)

(56) References Cited

U.S. PATENT DOCUMENTS 3,794,026 A 2/1974 Jacobs
3,808,706 A 5/1974 Mosley et al.
(Continued)

FOREIGN PATENT DOCUMENTS

AU 70522/96 1/1997
BR PI0809127-7 10/2019
(Continued)

OTHER PUBLICATIONS

Advisory Action corresponding to U.S. Appl. No. 13/464,752 dated Dec. 31, 2015.
(Continued)

*Primary Examiner* — Khadijeh A Vahdat
(74) *Attorney, Agent, or Firm* — Jenkins, Taylor & Hunt, P.A.; Robert J. Decker

(57) ABSTRACT

An aspect of various embodiments of the present invention system and method provide, but not limited thereto, a novel means for epicardial ablation using a double-curve steerable sheath and a double-curve deflectable open irrigated-tip/suction catheter that can be guided around the apex of the heart and adjusted so as to position the distal tip optimally. The catheter can also both deliver fluid to and withdraw fluid from the pericardial space. Access to the epicardial surface of the heart is via a subxiphoid entry. The method and means presented include, but are not limited to, steering, energy delivery, bipolar mapping, placement and use of electrodes, irrigation, suction of irrigation fluid, and other details of the subject invention.

15 Claims, 21 Drawing Sheets

Related U.S. Application Data

(60) Provisional application No. 60/906,689, filed on Mar. 13, 2007.

(52) U.S. Cl.
CPC ............... *A61B 2018/00035* (2013.01); *A61B 2018/00363* (2013.01); *A61B 2018/00577* (2013.01); *A61B 2018/1467* (2013.01); *A61B 2218/002* (2013.01); *A61B 2218/007* (2013.01)

(58) Field of Classification Search
CPC .......... A61B 2018/00363; A61B 2018/00577; A61B 2018/00791; A61B 2018/1467; A61B 2218/002; A61B 2218/007; A61M 2025/0681; A61M 2025/0133; A61M 2025/0147; A61M 2025/0662
USPC ...................................... 606/28–41
See application file for complete search history.

(56) References Cited

U.S. PATENT DOCUMENTS

| | | |
|---|---|---|
| 3,814,104 A | 6/1974 | Irnich et al. |
| 4,142,530 A | 3/1979 | Wittkampf |
| 4,167,070 A | 9/1979 | Orden |
| 4,263,918 A | 4/1981 | Swearingen et al. |
| 4,280,510 A | 7/1981 | O'Neill |
| 4,349,023 A | 9/1982 | Gross |
| 4,378,023 A | 3/1983 | Trabucco |
| 4,607,644 A | 8/1986 | Pohndorf |
| 4,817,634 A | 4/1989 | Holleman |
| 4,935,008 A | 6/1990 | Lewis, Jr. |
| 4,971,070 A | 11/1990 | Holleman |
| 4,991,603 A | 2/1991 | Cohen |
| 5,033,477 A | 7/1991 | Chin |
| 5,071,428 A | 12/1991 | Chin |
| 5,125,888 A | 6/1992 | Howard et al. |
| 5,158,097 A | 10/1992 | Christlieb |
| 5,176,153 A | 1/1993 | Eberhardt et al. |
| 5,213,570 A | 5/1993 | VanDeripe |
| 5,269,326 A | 12/1993 | Verrier |
| 5,300,110 A | 4/1994 | Latterell |
| 5,335,313 A | 8/1994 | Douglas |
| 5,336,252 A | 8/1994 | Cohen |
| 5,395,349 A | 3/1995 | Quiachon |
| 5,465,711 A | 11/1995 | Moll |
| 5,484,423 A | 1/1996 | Waskonig |
| 5,500,012 A | 3/1996 | Brucker et al. |
| 5,509,924 A | 4/1996 | Paspa |
| 5,544,654 A | 8/1996 | Murphy |
| 5,662,647 A | 9/1997 | Crow et al. |
| 5,669,882 A | 9/1997 | Pyles |
| 5,679,005 A | 10/1997 | Einstein |
| 5,702,438 A | 12/1997 | Avitall |
| 5,707,335 A | 1/1998 | Howard et al. |
| 5,725,504 A | 3/1998 | Collins |
| 5,733,280 A | 3/1998 | Avitall |
| 5,779,694 A | 7/1998 | Howard et al. |
| 5,779,699 A | 7/1998 | Lipson |
| 5,792,217 A | 8/1998 | Camps et al. |
| 5,797,870 A | 8/1998 | March |
| 5,800,428 A | 9/1998 | Nelson |
| 5,807,249 A | 9/1998 | Qin et al. |
| 5,812,978 A | 9/1998 | Nolan |
| 5,814,012 A | 9/1998 | Fleenor et al. |
| 5,827,216 A | 10/1998 | Igo |
| 5,843,048 A | 12/1998 | Gross |
| 5,846,239 A | 12/1998 | Swanson |
| 5,868,741 A | 2/1999 | Chia et al. |
| 5,885,217 A | 3/1999 | Gisselberg |
| 5,899,937 A | 5/1999 | Goldstein et al. |
| 5,916,194 A | 6/1999 | Jacobsen |
| 5,928,191 A | 7/1999 | Houser et al. |
| 5,931,810 A | 8/1999 | Grabek |
| 5,970,457 A | 10/1999 | Brant |
| 5,972,013 A | 10/1999 | Schmidt |
| 6,032,674 A | 3/2000 | Eggers et al. |
| 6,036,685 A | 3/2000 | Mueller |
| 6,051,008 A | 4/2000 | Saadat |
| 6,062,866 A | 5/2000 | Prom |
| 6,120,476 A | 9/2000 | Fung et al. |
| 6,123,084 A | 9/2000 | Jandak |
| 6,148,825 A | 11/2000 | Anderson |
| 6,156,009 A | 12/2000 | Grabek |
| 6,156,018 A | 12/2000 | Hassett |
| 6,162,195 A | 12/2000 | Igo |
| 6,200,303 B1 | 3/2001 | Verrior |
| 6,200,315 B1 * | 3/2001 | Gaiser ................ A61B 18/1492 606/41 |
| 6,206,004 B1 | 3/2001 | Schmidt |
| 6,206,874 B1 | 3/2001 | Ubby et al. |
| 6,216,030 B1 | 4/2001 | Howard et al. |
| 6,216,704 B1 | 4/2001 | Ingle et al. |
| 6,231,518 B1 | 5/2001 | Grabek |
| 6,234,804 B1 | 5/2001 | Yong |
| 6,237,605 B1 | 5/2001 | Vaska |
| 6,245,440 B1 | 6/2001 | Kuhlmann-Wilsdorf et al. |
| 6,263,241 B1 | 7/2001 | Rosborough |
| 6,266,567 B1 | 7/2001 | Ishikawa |
| 6,270,476 B1 | 8/2001 | Santoianni |
| 6,270,484 B1 | 8/2001 | Yoon |
| 6,272,370 B1 | 8/2001 | Gillies et al. |
| 6,273,877 B1 | 8/2001 | West |
| 6,278,975 B1 | 8/2001 | Brant |
| 6,298,259 B1 | 10/2001 | Kucharczyk et al. |
| 6,314,963 B1 | 11/2001 | Vaska |
| 6,322,536 B1 | 11/2001 | Rosengart |
| 6,325,776 B1 | 12/2001 | Anderson |
| 6,416,505 B1 | 7/2002 | Fleischman |
| 6,423,051 B1 | 7/2002 | Kaplan |
| 6,443,735 B1 | 9/2002 | Eggert |
| 6,500,130 B2 | 12/2002 | Kinsella |
| 6,527,767 B2 | 3/2003 | Wang |
| 6,551,289 B1 | 4/2003 | Higuchi |
| 6,554,809 B2 | 4/2003 | Aves |
| 6,558,382 B2 | 5/2003 | Jahns |
| 6,569,082 B1 | 5/2003 | Chin |
| 6,579,288 B1 | 6/2003 | Swanson et al. |
| 6,592,552 B1 | 7/2003 | Schmidt |
| 6,599,274 B1 | 7/2003 | Kucharczyk et al. |
| 6,602,242 B1 | 8/2003 | Fung et al. |
| 6,613,062 B1 | 9/2003 | Lechrone |
| 6,616,676 B2 | 9/2003 | Bashiri |
| 6,626,902 B1 | 9/2003 | Kucharczyk et al. |
| 6,666,844 B1 | 12/2003 | Igo |
| 6,666,861 B1 | 12/2003 | Grabek |
| 6,689,128 B2 | 2/2004 | Sliwa |
| 6,711,436 B1 | 3/2004 | Duhaylongsod |
| 6,723,092 B2 | 4/2004 | Brown |
| 6,752,805 B2 | 6/2004 | Maguire |
| 6,771,996 B2 | 8/2004 | Bowe |
| 6,783,510 B1 | 8/2004 | Gibson |
| 6,786,898 B2 | 9/2004 | Guenst |
| 6,811,544 B2 | 11/2004 | Schaer |
| 6,827,714 B2 | 12/2004 | Swanson |
| 6,827,715 B2 | 12/2004 | Francischelli |
| 6,834,201 B2 | 12/2004 | Gillies et al. |
| 6,835,193 B2 | 12/2004 | Epstein |
| 6,837,848 B2 | 1/2005 | Bonner |
| 6,837,886 B2 | 1/2005 | Collins |
| 6,849,075 B2 | 2/2005 | Bertolero |
| 6,868,291 B1 | 3/2005 | Bonner |
| 6,869,414 B2 | 3/2005 | Simpson |
| 6,874,501 B1 | 4/2005 | Estetter et al. |
| 6,876,885 B2 | 4/2005 | Swoyer |
| 6,899,710 B2 | 5/2005 | Hooven |
| 6,916,318 B2 | 7/2005 | Francischelli |
| 6,918,890 B2 | 7/2005 | Schmidt |
| 6,918,908 B2 | 7/2005 | Bonner |
| 6,921,295 B2 | 7/2005 | Sommer |
| 6,928,313 B2 | 8/2005 | Peterson |
| 6,936,040 B2 | 8/2005 | Kramm |
| 6,960,205 B2 | 11/2005 | Jahns |

(56) References Cited

U.S. PATENT DOCUMENTS

| | | |
|---|---|---|
| 6,968,223 B2 | 11/2005 | Hanover |
| 6,973,352 B1 | 12/2005 | Tsutsui |
| 6,974,454 B2 | 12/2005 | Hooven |
| 7,004,937 B2 | 2/2006 | Lentz |
| 7,008,418 B2 | 3/2006 | Hall |
| 7,027,876 B2 | 4/2006 | Casavant |
| 7,037,296 B2 | 5/2006 | Kadziauskas |
| 7,041,099 B2 | 5/2006 | Thomas |
| 7,048,733 B2 | 5/2006 | Hartley et al. |
| 7,059,878 B1 | 6/2006 | Hendrixson |
| 7,063,693 B2 | 6/2006 | Guenst |
| 7,085,606 B2 | 8/2006 | Flach |
| 7,089,063 B2 | 8/2006 | Lesh |
| 7,090,637 B2 | 8/2006 | Danitz |
| 7,101,362 B2 | 9/2006 | Vanney |
| 7,104,986 B2 | 9/2006 | Hovda |
| 7,120,504 B2 | 10/2006 | Osypka |
| 7,130,699 B2 | 10/2006 | Huff |
| 7,142,919 B2 | 11/2006 | Hine |
| 7,146,225 B2 | 12/2006 | Guenst |
| 7,147,633 B2 | 12/2006 | Chee |
| 7,207,988 B2 | 4/2007 | Leckrone |
| 7,214,180 B2 | 5/2007 | Chin |
| 7,226,448 B2 | 6/2007 | Bertolero |
| 7,226,458 B2 | 6/2007 | Kaplan |
| 7,232,422 B2 | 6/2007 | Gibson |
| 7,247,139 B2 | 7/2007 | Yudkovitch |
| 7,259,906 B1 | 8/2007 | Islam |
| 7,264,587 B2 | 9/2007 | Chin |
| 7,286,992 B2 | 10/2007 | Sander |
| 7,309,328 B2 | 12/2007 | Kaplan |
| 7,398,781 B1 | 7/2008 | Chin |
| 7,468,029 B1 | 12/2008 | Robertson |
| 7,473,244 B2 | 1/2009 | Frazier |
| 7,670,327 B2 | 3/2010 | Kucharczyk et al. |
| 7,727,225 B2 | 6/2010 | Broaddus et al. |
| 8,048,072 B2 | 11/2011 | Verin et al. |
| 8,096,984 B2 | 1/2012 | Kucharczyk et al. |
| 8,211,083 B2 | 7/2012 | Broaddus et al. |
| 8,226,694 B2 | 7/2012 | Broaddus et al. |
| 8,255,193 B2 | 8/2012 | Humphrey et al. |
| 8,271,095 B2 | 9/2012 | O'Sullivan |
| 8,282,565 B2 | 10/2012 | Mahapatra et al. |
| 8,655,798 B2 | 2/2014 | Humphrey et al. |
| 8,728,053 B2 | 5/2014 | Broaddus et al. |
| 8,906,056 B2 | 12/2014 | Gillies et al. |
| 9,211,405 B2 | 12/2015 | Mahapatra et al. |
| 9,218,752 B2 | 12/2015 | Gillies et al. |
| 9,314,265 B2 | 4/2016 | Mahapatra et al. |
| 9,364,660 B2 | 6/2016 | Howard et al. |
| 9,468,396 B2 | 10/2016 | Mahapatra et al. |
| 9,636,487 B2 | 5/2017 | Utz et al. |
| 9,642,534 B2 | 5/2017 | Mahapatra et al. |
| 10,166,066 B2 | 1/2019 | Mahapatra et al. |
| 10,702,335 B2 | 7/2020 | Mahapatra et al. |
| 11,058,354 B2 | 7/2021 | Mahapatra et al. |
| 11,083,381 B2 | 8/2021 | Mahapatra et al. |
| 2001/0001314 A1 | 5/2001 | Davison et al. |
| 2001/0020166 A1 | 9/2001 | Daly |
| 2001/0024735 A1 | 9/2001 | Kuhlmann-Wilsdorf et al. |
| 2001/0025178 A1 | 9/2001 | Mulier et al. |
| 2001/0039410 A1 | 11/2001 | Verrier |
| 2001/0056280 A1 | 12/2001 | Underwood et al. |
| 2002/0002372 A1 | 1/2002 | Jahns et al. |
| 2002/0019626 A1 | 2/2002 | Sharkey et al. |
| 2002/0045895 A1 | 4/2002 | Sliwa |
| 2002/0055714 A1 | 5/2002 | Rothschild |
| 2002/0058925 A1 | 5/2002 | Kaplan |
| 2002/0072737 A1 | 6/2002 | Belden |
| 2002/0077600 A1 | 6/2002 | Sirimanne |
| 2002/0082523 A1 | 6/2002 | Kinsella |
| 2002/0103430 A1 | 8/2002 | Hastings et al. |
| 2002/0161361 A1 | 10/2002 | Sherman |
| 2003/0028187 A1 | 2/2003 | Vaska |
| 2003/0065318 A1 | 4/2003 | Pendekanti |
| 2003/0069572 A1 | 4/2003 | Wellman |
| 2003/0114796 A1 | 6/2003 | Schmidt |
| 2003/0181855 A1 | 9/2003 | Simpson |
| 2003/0204171 A1 | 10/2003 | Kucharczyk et al. |
| 2004/0024397 A1 | 2/2004 | Griffin |
| 2004/0024413 A1 | 2/2004 | Lentz |
| 2004/0024435 A1 | 2/2004 | Leckrone |
| 2004/0033477 A1 | 2/2004 | Ramphal et al. |
| 2004/0034365 A1 | 2/2004 | Lentz |
| 2004/0064138 A1 | 4/2004 | Grabek |
| 2004/0068312 A1 | 4/2004 | Sigg et al. |
| 2004/0087831 A1 | 5/2004 | Michels |
| 2004/0087938 A1 | 5/2004 | Leckrone |
| 2004/0102804 A1 | 5/2004 | Chin |
| 2004/0126746 A1 | 7/2004 | Toly |
| 2004/0138526 A1 | 7/2004 | Guenst |
| 2004/0138527 A1 | 7/2004 | Bonner et al. |
| 2004/0138531 A1 | 7/2004 | Bonner |
| 2004/0147826 A1 | 7/2004 | Peterson |
| 2004/0176679 A1 | 9/2004 | Murphy et al. |
| 2004/0186507 A1 | 9/2004 | Hall |
| 2004/0215168 A1 | 10/2004 | Verrier |
| 2004/0216748 A1 | 11/2004 | Chin |
| 2004/0267303 A1 | 12/2004 | Guenst |
| 2004/0267326 A1 | 12/2004 | Ocel |
| 2005/0004514 A1 | 1/2005 | Hochman |
| 2005/0010205 A1* | 1/2005 | Hovda ............... A61B 18/1482 606/41 |
| 2005/0020914 A1 | 1/2005 | Amundson |
| 2005/0027243 A1 | 2/2005 | Gibson |
| 2005/0085769 A1 | 4/2005 | MacMahon |
| 2005/0096522 A1 | 5/2005 | Reddy et al. |
| 2005/0107678 A1* | 5/2005 | Bowe ................ A61B 18/1492 600/374 |
| 2005/0119556 A1 | 6/2005 | Gillies et al. |
| 2005/0154376 A1 | 7/2005 | Riviere |
| 2005/0215945 A1 | 9/2005 | Harris et al. |
| 2005/0234507 A1 | 10/2005 | Geske |
| 2005/0251094 A1 | 11/2005 | Peterson |
| 2005/0256368 A1 | 11/2005 | Klenk |
| 2005/0261673 A1 | 11/2005 | Bonner |
| 2005/0273006 A1 | 12/2005 | Stewart |
| 2005/0273144 A1 | 12/2005 | Lennox |
| 2006/0025705 A1 | 2/2006 | Whittaker |
| 2006/0025762 A1 | 2/2006 | Mohan |
| 2006/0041243 A1 | 2/2006 | Nayak |
| 2006/0052660 A1 | 3/2006 | Chin |
| 2006/0064056 A1 | 3/2006 | Coyle |
| 2006/0064058 A1 | 3/2006 | Coyle |
| 2006/0074397 A1 | 4/2006 | Shimada |
| 2006/0106442 A1 | 5/2006 | Richardson |
| 2006/0122591 A1 | 6/2006 | Keidar |
| 2006/0189840 A1 | 8/2006 | Walsh |
| 2006/0200002 A1 | 9/2006 | Guenst |
| 2006/0229490 A1 | 10/2006 | Chin |
| 2006/0247522 A1 | 11/2006 | McGee |
| 2006/0247672 A1 | 11/2006 | Vidlund |
| 2006/0259017 A1 | 11/2006 | Heil |
| 2006/0270900 A1 | 11/2006 | Chin |
| 2006/0271032 A1 | 11/2006 | Chin |
| 2007/0016068 A1 | 1/2007 | Grunwald |
| 2007/0016069 A1 | 1/2007 | Grunwald |
| 2007/0016070 A1 | 1/2007 | Grunwald |
| 2007/0016072 A1 | 1/2007 | Grunwald |
| 2007/0032796 A1 | 2/2007 | Chin-Chen |
| 2007/0038052 A1 | 2/2007 | Swoyer |
| 2007/0043397 A1 | 2/2007 | Ocel |
| 2007/0055142 A1 | 3/2007 | Webler |
| 2007/0198041 A1 | 8/2007 | Rupp |
| 2007/0270882 A1 | 11/2007 | Hjelle |
| 2008/0015625 A1 | 1/2008 | Ventura |
| 2008/0051671 A1 | 2/2008 | Broome |
| 2008/0051864 A1 | 2/2008 | Callas et al. |
| 2008/0091109 A1 | 4/2008 | Abraham |
| 2008/0097399 A1 | 4/2008 | Sachar |
| 2008/0108945 A1 | 5/2008 | Kaplan |
| 2008/0183080 A1 | 7/2008 | Abraham |
| 2008/0208184 A1 | 8/2008 | Davies |
| 2008/0262432 A1 | 10/2008 | Miller |

(56) References Cited

U.S. PATENT DOCUMENTS

| | | |
|---|---|---|
| 2008/0262467 A1 | 10/2008 | Humphrey et al. |
| 2008/0294174 A1 | 11/2008 | Bardsley |
| 2009/0030469 A1 | 1/2009 | Meiry |
| 2009/0048577 A1 | 2/2009 | Gillies et al. |
| 2009/0068627 A1 | 3/2009 | Toly |
| 2009/0069697 A1 | 3/2009 | Frazier |
| 2009/0192487 A1 | 7/2009 | Broaddus et al. |
| 2009/0246747 A1 | 10/2009 | Buckman |
| 2009/0253102 A1 | 10/2009 | Porikli et al. |
| 2009/0311656 A1 | 12/2009 | Lundback et al. |
| 2010/0042158 A1 | 2/2010 | Broaddus et al. |
| 2010/0069849 A1 | 3/2010 | Kassab |
| 2010/0094143 A1 | 4/2010 | Mahapatra |
| 2010/0114093 A1 | 5/2010 | Mahapatra |
| 2010/0167251 A1 | 7/2010 | Boutchko et al. |
| 2010/0210927 A1 | 8/2010 | Gillies et al. |
| 2010/0211064 A1 | 8/2010 | Mahapatra |
| 2010/0241185 A1 | 9/2010 | Mahapatra et al. |
| 2012/0249890 A1 | 10/2012 | Chardon et al. |
| 2012/0274863 A1 | 11/2012 | Chardon et al. |
| 2012/0278348 A1 | 11/2012 | Chardon et al. |
| 2012/0283582 A1 | 11/2012 | Mahapatra et al. |
| 2012/0310052 A1 | 12/2012 | Mahapatra |
| 2012/0330184 A1 | 12/2012 | Mahapatra |
| 2013/0085386 A1 | 4/2013 | Humphrey et al. |
| 2013/0090556 A1 | 4/2013 | Broaddus et al. |
| 2013/0096428 A1 | 4/2013 | Gillies et al. |
| 2013/0108999 A1 | 5/2013 | Gillies |
| 2013/0225904 A1 | 8/2013 | Gillies et al. |
| 2013/0303967 A1 | 11/2013 | Utz et al. |
| 2014/0128955 A1 | 5/2014 | Howard et al. |
| 2015/0297073 A1 | 10/2015 | Nguyen et al. |
| 2016/0100797 A1 | 4/2016 | Mahapatra et al. |
| 2016/0331445 A1 | 11/2016 | Mahapatra et al. |
| 2017/0086707 A1 | 3/2017 | Mahapatra et al. |
| 2017/0238823 A1 | 8/2017 | Mahapatra et al. |
| 2018/0361145 A1 | 12/2018 | Mahapatra et al. |

FOREIGN PATENT DOCUMENTS

| | | |
|---|---|---|
| CA | 2236958 | 5/1998 |
| CA | 2236958 | 11/1998 |
| DE | 43 13 903 C1 | 9/1994 |
| EP | 0134367 A1 | 3/1985 |
| EP | 0417171 B1 | 3/1991 |
| EP | 0 450 608 A1 | 10/1991 |
| EP | 1129681 A1 | 9/2001 |
| EP | 1 181 896 | 2/2002 |
| EP | 2279773 | 2/2011 |
| EP | 2134253 | 1/2022 |
| WO | WO 87/04081 | 7/1987 |
| WO | WO 93/20878 | 10/1993 |
| WO | WO 93/20886 | 10/1993 |
| WO | WO 95/10319 | 4/1995 |
| WO | WO 95/15115 | 6/1995 |
| WO | WO 97/33526 | 9/1997 |
| WO | WO1997/037847 | 10/1997 |
| WO | WO1998/00060 | 1/1998 |
| WO | WO 99/18869 | 4/1999 |
| WO | WO00/007652 | 2/2000 |
| WO | WO00/23000 | 4/2000 |
| WO | WO 01/05306 | 1/2001 |
| WO | WO 01/58373 | 8/2001 |
| WO | WO 01/68173 | 9/2001 |
| WO | WO 01/80724 | 11/2001 |
| WO | WO 01/80757 | 11/2001 |
| WO | WO 01/93930 | 12/2001 |
| WO | WO2002/074358 | 9/2002 |
| WO | WO 03/092792 A2 | 11/2003 |
| WO | WO06/15091 | 2/2006 |
| WO | WO06/089243 | 8/2006 |
| WO | WO 2006113267 | 10/2006 |
| WO | WO 2007/081842 | 7/2007 |
| WO | WO 2008/02595 | 1/2008 |
| WO | WO 2008/013709 | 1/2008 |
| WO | WO 2008/057370 | 5/2008 |
| WO | WO 2008/112870 | 9/2008 |
| WO | WO 2008/118737 | 10/2008 |
| WO | WO 2008/115745 | 11/2008 |
| WO | WO 2009/062061 | 5/2009 |
| WO | WO 2010127259 A1 | 11/2010 |
| WO | WO 2011/103456 | 8/2011 |
| WO | WO 2011102874 A1 | 8/2011 |
| WO | WO2011/160080 | 12/2011 |
| WO | WO/2012/065125 | 5/2012 |

OTHER PUBLICATIONS

Advisory Action Notice of Allowance corresponding to U.S. Appl. No. 12/530,938 dated May 12, 2016.

Aliot et al., "EHRA/HRS expert consensus on catheter albation of ventricular arrhythmias," Europace, vol. 11, No. 6, pp. 771-817, 2009.

Arrow International Corporation, AN-05505 Epidural Needle, www.arrowintl.com/products/boms/AN05505.asp?cat=17&item=AN-05505&xsec= {accessed Feb. 13, 2007).

Aupperle et al., "Ablation of Atrial Fibrillation and Esophageal Injury: Effects of Energy Source and Ablation Technique," Journal of Thoracic and Cardiovascular Surgery, vol. 130, No. 6, pp. 1549-1554,(2005).

Beukema, "Radiofrequency Ablation of Atrial Fibrillation in Patients Undergoing Concommitant Cardiac Surgery. First Experience," PACE, 1997, p. 1100, vol. 20 (Part II).

Derose, Jr., "Robotically Assisted Left Ventricular Epicardial Lead Implantation for Biventricular Pacing: the Posterior Approach," The Annals of Thoracic Surgery, 2004, p. 1472-1474, vol. 77.

DP25B-S Strain Gage Pagel Meter: User's Guide, OMEGA Engineering, Inc., 2002 (accessed Jul. 9, 2007), Stamford, CT. Online at http://www.omega.com/Manuals/manualpdf/M3598.pdf.

DP41B Universal Input Meter: User's Guide, OMEGA Engineering, Inc., 1996 (accessed Dec. 5, 2007), Stamford, CT. Online at http://www.omega.comManuals/manualpdf.M2544.pdf.

DPI 603 Portable Pressure Calibrator User Guide, OMEGA Engineering, Inc., 1996 (accessed Decembers, 2007), Stamford, CT. Online at http://www.omega.com/Manual.pdf/M2913.pdf.

D'Avila "Transthoracic Epicardial Catheter Ablation of Ventricular Tachycardia," Heart Rhythm, 2006, p. 1110-1111, vol. 3.

Frolich, "Pioneers in Epidural Needle Design," Anesthesia & Analgesia, 2001, p. 215-220, vol. 93.

Hansky, "Lead Selection and Implantation Technique for Biventricular Pacing," European Heart Journal Supplements, 2004, p. D112-D116, vol. 6, Supplement D.

Intent to Grant corresponding to European Patent Application No. 08743794.3 dated Feb. 18, 2021.

International Preliminary Report on Patentability, Written Opinion, and International Search Report corresponding to International Patent Application No. PCT/US2008/057626 dated Sep. 22, 2009.

International Search Report corresponding to International Application No. PCT/US2011025470 dated Nov. 3, 2011.

Klein, "Radiofrequency Ablation of Cardiac Arrhythmias," Scientific American Science & Medicine, 1994, p. 48-57.

Lin, "Catheter Microwave Ablation Therapy for Cardiac Arrhythmias," Bioelectromagnetics, 1999, p. 120-132, vol. 20.

Mahapatra, "Access Device and Manometric Monitoring System for Epicardial Electrophysiology: Improved Prototype and Use in Human Trials," Jan. 2008, Technical Report No. UVA/640419/MAE08/102.

Mahapatra, "Access Device and Manometric Monitoring System for Epicardial Electrophysiology: Improved Prototype and Use in Human Trials," Jul. 2007, Technical Report No. UVA/640419/MAE08/101.

Mahapatra, "Incidence and Predictors of Cardiac Perforation after Permanent Pacemaker Placement," Heart Rhythm, 2005, p. 907-911, vol. 2, No. 9.

Mair, "Epicardial Lead Implantation Techniques for Biventricular Pacing via Left Lateral Mini-Thoracotomy, Video-Assisted Thoracoscopy, and Robotic Approach," The Heart Surgery Forum #2003-4883, 2003, p. 412-417, vol. 6 (5).

(56) References Cited

OTHER PUBLICATIONS

Moses, "Sirolimus-Eluting Stents Versus Standard Stents in Patients with Stenosis in a Native Coronary Artery," New England Journal of Medicine, 2003, p. 1315-1323, vol. 349, No. 14.
Müller et al., "Application of CVD-diamond for catheter ablation in the heart," Diamond and Related Materials, vol. 13, pp. 1080-1083 (2004).
Notice of Allowance corresponding to corresponding to Brazilian Patent Application No. PI0809127-7 dated May 27, 2019.
Notice of Allowance corresponding to U.S. Appl. No. 12/530,830 dated Jun. 11, 2012.
Notice of Allowance corresponding to U.S. Appl. No. 12/530,860 dated Apr. 22, 2013.
Notice of Allowance corresponding to U.S. Appl. No. 12/530,938 dated Oct. 30, 2018.
Notice of Allowance corresponding to U.S. Appl. No. 12/532,233 dated Apr. 2, 2015.
Notice of Allowance corresponding to U.S. Appl. No. 13/464,752 dated Jan. 6, 2017.
Notice of Allowance corresponding to U.S. Appl. No. 13/464,762 dated Aug. 3, 2016.
Notice of Allowance corresponding to U.S. Appl. No. 13/607,993 dated Dec. 8, 2015.
Notice of Allowance corresponding to U.S. Appl. No. 14,879,849 dated Mar. 10, 2021.
Notice of Allowance corresponding to U.S. Appl. No. 14,879,849 dated Sep. 16, 2019.
Notice of Allowance corresponding to U.S. Appl. No. 14/967,923 dated Feb. 24, 2020.
Notice of Allowance corresponding to U.S. Appl. No. 15/295,102 dated Jan. 25, 2021.
Notice of Allowance corresponding to U.S. Appl. No. 15/589,522 dated Dec. 16, 2020.
Notice of Allowance corresponding to U.S. Appl. No. 15/589,522 dated Mar. 24, 2021.
Notification of Transmittal of International Preliminary Report on Patentability corresponding to PCT/US2008/056643 dated Aug. 19, 2009.
Office Action (Advisory Action) corresponding to U.S. Appl. No. 13/464,762 dated Dec. 17, 2015.
Office Action (Restriction Requirement) corresponding to corresponding to U.S. Appl. No. 13/464,762 dated May 23, 2013.
Office Action (Restriction Requirement) corresponding to U.S. Appl. No. 12/530,938 dated Mar. 21, 2012.
Office Action (Restriction Requirement) corresponding to U.S. Appl. No. 12/741,710 dated Aug. 22, 2012.
Office Action (Restriction Requirement) corresponding to U.S. Appl. No. 13/464,762 dated May 23, 2013.
Office Action (Restriction Requirement) corresponding to U.S. Appl. No. 14,879,849 dated Apr. 25, 2018.
Office Action (Restriction Requirement) corresponding to U.S. Appl. No. 15/960,137 dated Nov. 26, 2019.
Office Action corresponding to Brazilian Patent Application No. PI0809127-7 dated Nov. 27, 2018.
Office Action corresponding to European Patent Application No. 10846297.9 dated Jul. 1, 2014.
Office Action corresponding to U.S. Appl. No. 13/464,752 dated Dec. 4, 2014.
Office Action corresponding to U.S. Appl. No. 14/967,923 dated May 14, 2018.
Office Action corresponding to U.S. Appl. No. 14/967,923 dated Nov. 19, 2018.
Office Action corresponding to U.S. Appl. No. 12/530,860 dated Oct. 5, 2012.
Office Action corresponding to U.S. Appl. No. 12/530,938 dated Dec. 4, 2014.
Office Action corresponding to U.S. Appl. No. 12/530,938 dated Feb. 26. 2013.
Office Action corresponding to U.S. Appl. No. 12/530,938 dated Jun. 25, 2012.
Office Action corresponding to U.S. Appl. No. 12/530,938 dated Nov. 21, 2013.
Office Action corresponding to U.S. Appl. No. 12/530,938 dated Sep. 30, 2015.
Office Action corresponding to U.S. Appl. No. 12/532,233 dated Aug. 14, 2015.
Office Action corresponding to U.S. Appl. No. 12/532,233 dated Aug. 7, 2014.
Office Action corresponding to U.S. Appl. No. 12/532,233 dated Mar. 7, 2012.
Office Action corresponding to U.S. Appl. No. 12/532,233 dated May 15, 2013.
Office Action corresponding to U.S. Appl. No. 12/532,233 dated Oct. 26, 2012.
Office Action corresponding to U.S. Appl. No. 12/741,710 dated Apr. 22, 2014.
Office Action corresponding to U.S. Appl. No. 12/741,710 dated Jul. 3, 2013.
Office Action corresponding to U.S. Appl. No. 12/741,710 dated Jun. 15, 2015.
Office Action corresponding to U.S. Appl. No. 12/741,710 dated Nov. 8, 2012.
Office Action corresponding to U.S. Appl. No. 13/464,752 dated Aug. 2, 2016.
Office Action corresponding to U.S. Appl. No. 13/464,752 dated Jul. 10, 2015.
Office Action corresponding to U.S. Appl. No. 13/464,752 dated Mar. 7, 2014.
Office Action corresponding to U.S. Appl. No. 13/464,762 dated Aug. 25, 2015.
Office Action corresponding to U.S. Appl. No. 13/464,762 dated Jul. 16, 2013.
Office Action corresponding to U.S. Appl. No. 13/464,762 dated Mar. 2, 2016.
Office Action corresponding to U.S. Appl. No. 13/464,762 dated Mar. 6, 2014.
Office Action corresponding to U.S. Appl. No. 13/464,762 dated Nov. 12, 2014.
Office Action corresponding to U.S. Appl. No. 13/579,882 dated Jan. 13, 2015.
Office Action corresponding to U.S. Appl. No. 13/607,993 dated Aug. 14, 2014.
Office Action corresponding to U.S. Appl. No. 13/607,993 dated Jan. 12, 2015.
Office Action corresponding to U.S. Appl. No. 14,879,849 dated Aug. 5, 2020.
Office Action corresponding to U.S. Appl. No. 14,879,849 dated May,1 2019.
Office Action corresponding to U.S. Appl. No. 14,879,849 dated Sep. 10, 2018.
Office Action corresponding to U.S. Appl. No. 15/295,102 dated Jul. 9, 2020.
Office Action corresponding to U.S. Appl. No. 15/295,102 dated Jun. 13, 2019.
Office Action corresponding to U.S. Appl. No. 15/295,102 dated Sep. 28, 2018.
Office Action corresponding to U.S. Appl. No. 15/589,522 dated Feb. 21, 2020.
Office Action corresponding to U.S. Appl. No. 15/589,522 dated Jul. 8, 2019.
Office Action corresponding to U.S. Appl. No. 15/960,137 dated Feb. 12, 2020.
Office Action corresponding to U.S. Appl. No. 15/960,137 dated Sep. 28, 2020.
Patent Board Decision corresponding to U.S. Appl. No. 12/530,938 dated Sep. 25, 2018.
Patent Board Decision corresponding to U.S. Appl. No. 12/741,710 dated Feb. 22, 2018.
Petersen et al., "Mechanisms for Enlarging Lesion Size During Irrigated Tip Radiofrequency Ablation: Is There a Virtual Electrode Effect?" Journal of Interventional Cardiology, vol. 17, No. 3, pp. 171-177 (2004).

(56) References Cited

OTHER PUBLICATIONS

PX26 Series Pressure Transducers: Instruction Sheet, OMEGA Engineering, Inc., 2004 (accessed Dec. 5, 2007), Stamford, CT. Online at http:www.omega.com/Manualpdf/M1608.pdf.
S. Mahapatra, J. Tucker-Schwartz, "Pressure frequency characteristics of the pericardial space and thorax during subxiphoid access for epicardial ventricular tachycardia ablation," Heart Rhythm, vol. 7, No. 5, pp. 604-609, 2010.
Sarabanda, "Efficacy and Safety of Circumferential Pulmonary Vein Isolation Using a Novel Cryothermal Balloon Ablation System," Journal of the American College of Cardiology, 2005, p. 1902-1912, vol. 46, No. 10.
Scanavacca et al., "Catheter Ablation of Atrial Fibrillation. Techniques and Results," Arquivos Brasileiros de Cardiologia, vol. 85, No. 4, 7 pps., (2005).
Schwartzman et al., "Catheter Ablation of Ventricular Tachycardia Associated with Remote Myocardial Infarction: Utility of the Atrial Transseptal Approach," Journal of Interventional Cardiac Electrophysiology, vol. 1, pp. 67-71 (1997).
Sosa et al., "Nonsurgical transthoracic epicardial catheter ablation to treat recurrent ventricular tachycardia occuring late after myocardial infarction," J. Am. Coll. Cardiol., vol. 35, No. 6, pp. 1442-1449, 2000.
Sosa, "Epicardial Mapping and Ablation Techniques to Control Ventricular Tachycardia," Journal of Cardiovascular Electrophysiology, 2005, p. 449-452, vol. 16, No. 4.
Sosa, "Nonsurgical Transthoracic Epicardial Approach in Patients with Ventricular Tachycardia and Previous Cardiac Surgery," Journal of Interventional Cardiac Electrophysiology, 2004, p. 281-288, vol. 10.
Sosa, "Percutaneous Pericardia! Access for Mapping and Ablation of Epicardial Ventricular Tachycardias," Circulation, Journal of the American Heart Association, 2007, p. e542-e544, vol. 115.
Stokes, U.S. Statutory Invention Registration H356, Nov. 3, 1987.
Thomas, "Analysis of Human Epidural Pressures," Regional Anesthesia, 1992, p. 212-215, vol. 17, No. 4.
Tomaske, "Do Daily Threshold Trend Fluctuations of Epicardial Leads Correlate with Pacing and Sensing Characteristics in Paediatric Patients," Europace, 2007, p. 662-668, vol. 9.
Tucker-Schwartz et al., "Pressure-Frequency Sensing Subxiphoid Access System for Use in Percutaneous Cardiac Electrophysiology: Prototype Design and Pilot Study Results," IEEE Transactions on Biomedical Engineering, vol. 56, pp. 1160-1168 (May 2009).
Tungjitkusolmun et al., "Finite Element Analyses of Uniform Current Density Electrodes for Radio-Frequency Cardiac Ablation," IEEE Transactions on Biomedical Engineering, vol. 47, No. 1, pp. 32-40, (2000).
Written Opinion of the International Searching Authority corresponding to PCT/US2008/056643 dated Aug. 22, 2008.
Decision to Grant corresponding to European Patent Application No. 08743794.3 dated Jan. 7, 2022.
Intent to Grant corresponding to European Patent Application No. 08743794.3 dated Aug. 27, 2021.
Notice of Allowance corresponding to U.S. Patent Application Serial No. 15/295, 102 dated Jul. 21, 2021.
Notice of Allowance corresponding to U.S. Appl. No. 15/295,102 dated Jun. 2, 2022.
Notice of Allowance corresponding to U.S. Patent Application Serial No. 15/295, 102 dated Sep. 15, 2022.
Office Action corresponding to U.S. Appl. No. 15/295,102 dated Nov. 18, 2021.
Office Action corresponding to U.S. Appl. No. 15/960,137 dated Dec. 7, 2021.
Office Action corresponding to U.S. Patent Application Serial No. 15/960, 137 dated Jun. 16, 2022.
Grimard et al.,(2010) "Percutaneous epicardial radiofrequency ablation of ventricular arrhythmias after failure of endocardial epproach: a 9-year experience," J. Cardiovasc. Electrophysiol., vol. 21, No. 1, pp. 56-61.
Notice of Allowance corresponding to U.S. Appl. No. 15/295,102 dated Mar. 2, 2023.
Notice of Allowance corresponding to U.S. Appl. No. 16/236,664 dated Dec. 8, 2022.
Office Action corresponding to U.S. Appl. No. 15/960,137 dated Jan. 17, 2023.
Packer, (2005) "Multimodality 3-D Ultrasound and Computed Tomographic Image Fusion: A Novel Basis for Catheter Navigation and Electroanatomic Mapping,", Cirulation, Clinical Science, Supplement 11, vol. 112, No. 17, p. 2939.
Sacher et al (2009) "Prevalence of epicardial scar in patients referred for ventricular tachycardia ablation," Heart Rhythm, vol. 6, pp. S175-6. [Abstract].
Sosa et al., (1998) "Endocardial and epicardial ablation guided by nonsurgical transthoracic epicardial mapping to treat recurrent ventricular tachycardia," J. Cardiovasc. Eletrophysiol., vol. 9, No. 3, pp. 229-39
Tucker-Schwartz et al.,(2011) "Improved Pressure-Frequency Sensing Subxiphoid Pericardial Access System: Performance Characteristics During in Vivo testing," IEEE Transactions on Biomedical Engineering, vol. 58, pp. 845-852.
U. Tedrow and W. Stevenson,(2009) "Strategies for epicardial mapping and ablation of ventricular tachycardia," J. Cardiovasc. Electrophysiol., vol. 20, No. 6, pp. 710-3.
Zei et al., "Epicardial Catheter Mapping and Ablation of Ventricular Tachycardia," Heart Rhythm, vol. 3, pp. 360-363, (2006).
Office Action corresponding to U.S. Appl. No. 15/960,137 dated Jul. 18, 2023.

\* cited by examiner

EPICARDIAL ABLATION CATHETER AND METHOD OF USE

RELATED APPLICATIONS

The present application is a continuation application of U.S. application Ser. No. 12/530,938, filed Sep. 11, 2009, now U.S. Pat. No. 10,166,066 which is a national stage filing of International Application No. PCT/US2008/056816, filed Mar. 13, 2008, which claims priority under 35 U.S.C. § 119(e) from U.S. Provisional Application Ser. No. 60/906,689 filed Mar. 13, 2007, entitled "Epicardial Ablation Catheter and Access Sheath and Method of Use," the disclosures of which are hereby incorporated by reference herein in their entireties.

This application is related to International Application No. Serial No. PCT/US2008/056643, filed Mar. 12, 2008, entitled, "Access Needle Pressure Sensor Device and Method of Use," (and its corresponding U.S. National Stage application Ser. No. 12/530,830, filed Sep. 11, 2009, now U.S. Pat. No. 8,282,565) which claims benefit under 35 U.S.C. § 119(e) of priority from U.S. Provisional Application Ser. No. 60/918,782, filed Mar. 19, 2007, entitled "Manometrically Monitored Introducer Needle and Method of Use," the disclosures of which are hereby incorporated by reference herein in their entirety.

FIELD OF THE INVENTION

The invention is in the field of medical implants. More specifically, the invention relates to an apparatus and means for treating cardiac arrhythmias. Most exactly, the invention provides for a novel means and method of ablating epicardial tissues with a novel catheter and sheath and technique of use.

BACKGROUND OF THE INVENTION

Cardiac arrythmias are frequently treated with electrophysiology procedures and ablation. In the U.S., Europe and Japan during the last 20 years most of these procedures have been performed endocardially (inside the heart) with catheters that have been navigated from leg and neck veins into the heart chambers. To some degree this is a historical accident. Initially ablation was done primarily for simple supraventricular tachycardias that have their focus on or near the endocardium. However, the fastest growing procedures are those done to treat atrial fibrillation (AF) and ventricular tachycardia (VT), which both have a major component on the epicardium. In fact, the now common pulmonary vein isolation ablation procedure to cure AF, which is done endocardially, actually targets epicardial fibers. Energy is delivered endocardially at a level that is sufficient to penetrate the atrial tissue and destroy the responsible epicardial fibers. However, ablating from inside the heart in order to target the outside tissues has risks, including stroke, and may require more energy than when these fibers are ablated directly from the epicardial side. AF ablation is now performed routinely at academic centers and is entering the mainstream of cardiological practice. It will soon become even more widely used because the American Heart Association recently issued a guideline that upgraded pulmonary vein isolation for AF to a first-line therapy.

Similarly, ablation of ventricular tachycardia (VT), while relatively rare now, is becoming more common as more patients are now surviving heart failure due to implantable cardiac defibrillators and improved medicines. The substrate in VT ablation is epicardial in 23-50% of patients. Ablation for this purpose is typically performed endocardially as well, with the goal of delivering energy transmurally across 10-15 mm of ventricle to destroy fibers epicardially. However, some care centers do perform the ablation epicardially, but there are barriers.

A major barrier to clinical adoption of epicardial ablation is the lack of tools, specifically catheters and sheaths, designed for use specifically in epicardial procedures. While there are a myriad ablation catheters for endocardial ablation, to our knowledge no ablation catheter has been developed specifically for epicardial ablation. Thus, practitioners of epicardial ablation are forced to use endocardial tools despite the many differences in the practice of endocardial and epicardial ablation.

The prior art is silent on the teaching of novel catheters designed specifically for epicardial ablation. The extant prior art that defines the present standard of care therefore has several significant limitations when viewed from the vantage point of the medical devices needed for an epicardial ablative procedure.

In the standard endocardial approach, access to the heart is obtained by inserting a sheath and catheter into the leg veins and then navigating the sheath up the entire vena cava into the right atrium, and then gently curving into the rest of the heart.

Another limitation of the prior art has to do with the geometry of the existing devices. In the endocardial approach there is one only turn that must be made; from the vena cava to the right atrium. This curve is gentle. Other areas of the heart can be reached by moving inside of the chamber of the heart. Thus, there is room to turn and as a result, endocardial sheaths and catheters have only a single adjustable curve. However, in the pericardium there is little room to move, which limits the ability to maneuver. When carrying out a subxiphoid access, there are three separate turns that must be made: (1) A 90 degree turn immediately after entering the pericardial space, (2) a 130 degree (approximate and variable) at the apex of the heart, and (3) a final positioning turn (variable) right at the ablation side.

In conventional practices, for example, these turns are made by pushing and then bouncing a standard catheter against the heart and pericardium in order to force the catheter in the correct direction. This is not ideal since it could lead to injury and might also easily unravel the device during positioning.

Another deficiency with conventional catheters is that no irrigated-tip devices built for epicardial use exist. Animal studies show that irrigated tip catheters make deeper, larger lesions than non-irrigated-tip catheters. In particular externally-irrigated (open) tips, where cool saline is infused near the tip of the ablation catheter, make the deepest lesions. Thus, many centers prefer irrigated tips infusing saline at 17 cc/min in ablation of AF and VT. However, irrigation during epicardial ablation means infusing saline into the limited pericardial space. An infusion of even 100 cc (corresponding to just under 6 minutes of ablation if the infusion rate is 17 cc/min) is enough to cause themodynamic collapse due to pericardial tamponade. Even smaller fluid levels can make epicardial ablation difficult by making the catheter float in a sea of fluid. These are the reasons that Stevenson and Sosa, experts in ablation, have written that externally-irrigated tips are to be avoided epicardially. Sosa E, Scanavacca M. Epicardial Mapping and Ablation Techniques to Control of Ventricular Tachycardia. Journal of Cardiovascular Electrophysiology 16:449-452, 2005; Zei P, Stevenson W. Epicardial Catheter Mapping and Ablation of Ventricular Tachycardia Heart Rhythm 3:360-363; 2006.

Another limitation of conventional ablation catheters is that they provide energy in all directions. As a result, anything continually touching the catheter while ablating is damaged. Inside the heart this is reasonable since one side of the catheter is placed against the target heart tissue and the rest of the catheter is surrounded by moving blood. Thus the fixed target is burned but the moving blood is not damaged. Epicardially, however, there is no moving blood. Thus, when placing the catheter against the target the rest of the catheter may touch adjacent structures such as esophagus, lung or phrenic nerve, which are all stationary structures that could be damaged.

Thus, an aspect of the present invention epicardial catheter shall be the ability to direct its energy in one direction.

Another limitation in conventional catheters is that the trend has been to make the ablation tip longer. Initially ablation tips were 4 mm in length. They have since grown to 8 mm or, in some cases, even 10 mm long. While these larger tips have been shown to make deeper lesions in the endocardium due to blood cooling the large tip, there is no blood in the epicardium. Furthermore, in the endocardial space the catheter floats in the chamber and only a small part of an 8 mm tip will have contact with the endocardium, and thus the lesion can be specific to where there is contact. However, on the epicardium the pericardium will push the entire tip onto the epicardium and lead to a non-specific lesion. In addition, while larger tips make a larger lesion when the tip is non-irrigating, animal studies have shown that smaller tips make better lesions when the tip is irrigating.

Accordingly, an aspect of an embodiment of the present invention provides a catheter that will have a smaller tip, such as about 2 mm tip.

There is therefore a need in the art for an effective epicardial ablation catheter to provide improved means of treatment with regard to each of the heretofore discussed limitations in the prior art. The present invention provides a solution to the problems currently faced by these limitations. The advantages and features of the invention disclosed herein will be made more apparent from the description, drawings, and claims that follow.

BRIEF SUMMARY OF INVENTION

To traverse the limitations of the prior art, an aspect of various embodiments of the present invention system and method provide, but are not limited thereto, a means for employing an irrigated-tip, epicardial ablation catheter that has been introduced into the chest via a subxiphoid point of entry. Paired with this embodiment would be a double lumen sheath with two points of deflection.

An aspect of the present invention, among other things, serves to introduce such an epicardial sheath and ablation catheter to the art.

With present invention epicardial access a needle-stick is made in the subxiphoid area of the chest and the ablation device must then only be advanced a short distance to get to the heart. However, it must immediately be steered through an acute angle to avoid the heart itself. Because of this, aspects of the present invention devices and those used in conventional techniques can be contrasted. For instance, conventional endocardial catheters are typically 100 cm in length or longer since they must go from the leg to the heart, while an embodiment of the present invention epicardial sheath could be, for example, about 30 cm or less since it may only need to go from the chest to the heart. Similarly, sheaths in excess of the required 30 cm could be an awkward physical obstacle that would interfere with the procedure and, if inadvertently bumped or moved, could injure the patient. Similarly the conventional long catheters used in endocardial ablation, while not dangerous as such, are nevertheless awkward. Another reason that present invention shorter catheters may be preferred in epicardial procedures is that it is easier to effect rotation of the distal end of a catheter through rotation of the proximal end if the length of the catheter is shorter. Therefore, a shorter sheath and catheter would be less awkward, easier to use, and safer.

An aspect of an embodiment of the present invention enables the sheath and catheter to make these turns without the pushing and bouncing which accompanies the use of conventional catheters. An aspect of an embodiment of the present invention provides, for example, a catheter and sheath which each have two adjustable curved sections in their structures. Thus, four separate and distinct turns could be made (one more than is needed.) Because each device would have two adjustable curves, each could be used independently with a standard single curve catheter and still get three points of deflection. However the curvature of an epicardial sheath has to be broad since it must turn around the underside of the heart. Thus, an exemplary present invention system (catheter or sheath) for ablation would have two curves: the proximal curve, closer to the doctor, would be a unidirectional broad curve with a relatively large radius of curvature, while the distal curve, further from the doctor, would be a tighter, with a relatively small radius of curvature.

An aspect of an embodiment of the present invention solves the problem posed by the use of irrigated tips by use of a separate suction channel that allows for removal of the irrigation fluid from the pericardium at a rate sufficient to overcome the problems related to the infusion of the liquid. Another advantage of suction associated with an aspect of an embodiment of the present invention would arise if there was a perforation of the heart, which occurs in 2% of patients during AF ablations. In such cases, the fluid could be sucked out, thus preventing hemodynamic collapse and death.

The insertion of the sheath into the epicardial region may be aided by the use of an access needle and subsequent passage of a guidewire. The access needle may first be inserted into the epicardium, with the guidewire then put in place. The sheath may then be coaxaially slid over the guidewire to access the epicardial region. After positioning the sheath in the desired position, the catheter may then be inserted through the sheath to reach the epicardium.

It should be appreciated that the guidewire (or any component mentioned) may be removed or replaced as desired or required for the applicable medical procedure or applicable anatomy.

An aspect of an embodiment of the present invention provides an ablation catheter system for ablation of epicardial tissue of a heart of a subject. The system comprising: an ablation catheter comprising a distal end, proximal end, and longitudinal wall there between and one or more electrodes in communication with the ablation catheter. Further, the ablation catheter includes one or more distal irrigation apertures at the distal end, wherein the distal irrigation apertures in communication with one or more irrigation lumens extending longitudinally toward the proximal end; and/or one or more distal suction apertures at the distal end, wherein the distal suction apertures in communication with one or more suction lumens extending longitudinally toward the proximal end.

An aspect of an embodiment of the present invention provides a method for ablating epicardial tissue of a heart of a subject. The method comprising: ablating the epicardial tissue of the heart using one or more electrodes on an ablation catheter. Further the method comprises: irrigating in a region of the epicardial tissue; and/or suctioning in a region of the epicardial tissue.

An aspect of various embodiments of the present invention system and method provide, but not limited thereto, a novel means for epicardial ablation using a double-curve steerable sheath and a double-curve deflectable open irrigated-tip/suction catheter that can be guided around the apex of the heart and adjusted so as to position the distal tip optimally. It should be appreciated that more curves on the sheath and catheter (guide wire, leads, etc.) may be implemented if desired or required. The catheter can also both deliver fluid (or applicable medium) to and withdraw fluid (or applicable medium) from the pericardial space (or applicable region or space). Access to the epicardial surface of the heart may be via a subxiphoid entry. The method and means presented include, but are not limited to, steering, energy delivery, bipolar mapping, placement and use of electrodes, irrigation, suction of irrigation fluid, and other details of the subject invention.

Those skilled in the art will recognize that significant advantages accrue from the use of the means and method of the invention, because it foresees novel and previously untaught techniques for the ablation of arrhythmia-producing cardiac tissues.

BRIEF DESCRIPTION OF THE DRAWINGS

The foregoing and other objects, features and advantages of the present invention, as well as the invention itself, will be more fully understood from the following description of preferred embodiments, when read together with the accompanying drawings in which.

DETAILED DESCRIPTION OF THE EXEMPLARY EMBODIMENTS

In order to more clearly and concisely describe the subject matter of the claims, the following definitions are intended to provide guidance as to the meaning of specific terms used in the following written description, examples, and appended claims.

As used herein, the term 'sealant device' means any thin-walled structure that separates the interior annular space between catheter and sheath from the outside, thereby preventing leakage.

As used herein, the term 'tensioning means' may include a steering means comprised of wires, rods, chains, bands, chords, ropes, string tubes, filaments, threads, fibers, strands, or any other extended elements.

When describing materials, temperature sensors such as thermocouples, thermistors, fiber optic sensors, resistive temperature devices, semiconductor temperature sensors, and any other temperature transducers that can sense the thermal characteristics of the system are suitable for use herein.

Furthermore, side channels and suction outlets may include proximal irrigation and suction apertures respectively. Each of these elements may be embodied in any number of forms, including a branch channel, a side channel, a connector, a port hole, an outlet, a window, or any other point of ingress or egress.

Likewise, suction and irrigation apertures and holes may be embodied in any number of forms, including a branch channel, a side channel, a connector, a port hole, an outlet, a window, or any other point of ingress or egress.

Other equivalent structures would also be suitable in each of the above examples. Identification of equivalents is well within the skill of the ordinary practitioner and would require no more than routine experimentation.

Similarly, by means of example and not limitation it should be recognized that the length of the distal tip and the distal segment can be increased or decreased as desired or required according to the subject anatomy and ablation procedure.

Practice of the invention will be still more fully understood from the following examples, which are presented herein for illustration only and should not be construed as limiting the invention in any way.

Figure 1:
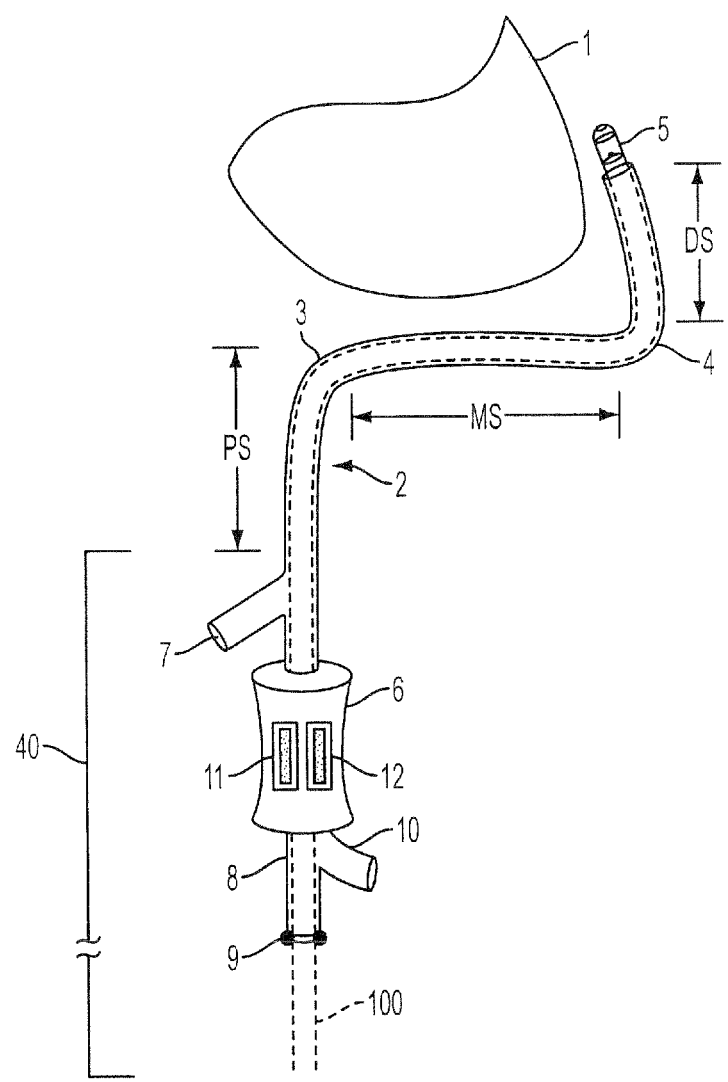
FIG. 1 is a schematic illustration of an embodiment of the overall structure of the epicardial ablation sheath and catheter, relative to the heart.

FIG. 1 shows the apex region of a human heart 1 around the tip of which the ablation sheath 2 may be steered, in order to position the catheter's distal tip 5 at a preferred epicardial location for ablative therapy. The overall length of the sheath/catheter portion of the device may be approximately 30 cm. The length may vary as desired or required according to the medical procedure and the anatomy. The proximal segment (referred to as PS), which may extend from a suction outlet 7 to the proximal center of curvature 3 may be about 10 cm. The medial segment (referred to as MS), which may extend from the proximal center of curvature 3 to the distal center of curvature 4 may be about 15 cm. The distal segment (referred to as DS), which terminates at the distal tip 5 may be about 5 cm. The proximal end of the sheath is affixed to the control handle 6 for the device. The handle may have two tension controls 11, 12 which are used to adjust the proximal and distal curvatures of the sheath at its two centers of curvature. On the proximal side of the control handle 6 is a three-way channel 8 the side-channel 10 of which is used as the inlet for an irrigation fluid such as saline solution that can be pumped through the distal end port of the catheter. The other channel has a sealing diaphragm 9 through which the ablation catheter 100 itself is inserted and which seals against it.

An aspect of an embodiment of the present invention ablation system may be implemented with an access needle (introducer needle), conduit or the like. The access needle or conduit is adapted to be inserted into the epicardial region or other body part or body space so as to provide an access or guideway for the present invention ablation catheter, sheath, guidewire, etc. An example of an access system is disclosed in PCT International Application No. Serial No. PCT/US2008/056643, filed Mar. 12, 2008, entitled, "Access Needle Pressure Sensor Device and Method of Use," of which is hereby incorporated by reference herein in its entirety. See for example, but not limited thereto, FIGS. 2 and 5 of the PCT International Application No. Serial No. PCT/US2008/056643. The access needle sensor device or the like serves as a guideway for introducing other devices into the pericardium, for instance sheath catheters that might subsequently be employed for procedures in the periardium and the epicardium of the heart, or other applicable regions, space or anatomy. Other devices that the access device may accommodate with the practice of this invention include, but not limited thereto, the following: ablation catheters, guidewires, pacing leads, pacing catheters, pacemakers, visualization and recording devices, drugs, lumens, steering devices or systems, drug or cell delivery catheters, fiber endoscopes, suctioning devices, irrigation devices, electrode catheters, needles, optical fiber sensors, sources of illumination, vital signs sensors, and the like Theses devices may be deployed for procedures in an integral body part or space.

Further, it should be appreciated that the present invention ablation system may be inserted into a subject via an interventional procedure or a surgical procedure, as well as a combination thereof.

The proximal end 40 of the catheter 100 may be implemented as desired or required along any point or segment, for example, as illustrated by the bracket in FIG. 1. It should be appreciated that the proximal end may include, for example: a point at the proximal tip of the cathode; a portion or segment at or in the vicinity of the proximal tip of the cathode; or a portion or segment leading up to (or partially up to but not all the way up to) the proximal tip of the cathode. The length and location may vary as desired or required in order to practice the invention according to medical procedures and anatomical considerations. In summary, the proximal end may be translated in the proximal or distal direction on a case by case basis.

Similarly, it should be appreciated that the distal end may include, for example: a point at the distal tip of the cathode; a portion or segment at or in the vicinity of the distal tip of the cathode; or a portion or segment leading up to (or partially up to but not all the way up to) the distal tip of the cathode. The length and location may vary as desired or required in order to practice the invention according to medical procedures and anatomical considerations. In summary, the distal end may be translated in the proximal or distal direction on a case by case basis.

Figure 2C:
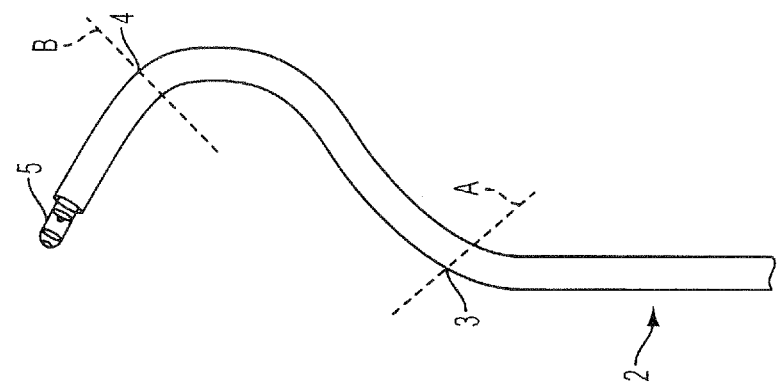
FIGS. 2(A)-2(C) are schematic illustrations of an embodiment of the device being mechanically aligned for delivery of an ablative treatment in un-tensioned, partial steering, and full steering modes, respectively.
Figure 2B:
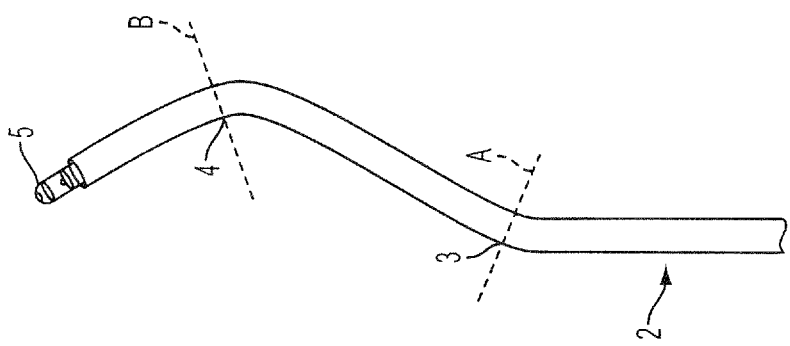
Figure 2A:
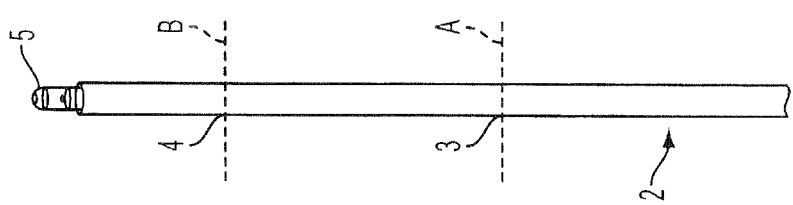

FIG. 2(A) shows the un-tensioned ablation sheath 2 with the distal tip 5 of the catheter 100 extending through it. The proximal center of curvature 3 is indicated by the line A, and the distal center of curvature 4 is indicated by the line B. FIG. 2(B) shows the configuration of the device after partial steering of sheath around the two centers of curvature. FIG. 2(C) shows the configuration of the device after full steering of the sheath around the two centers of curvature.

Figure 3A:
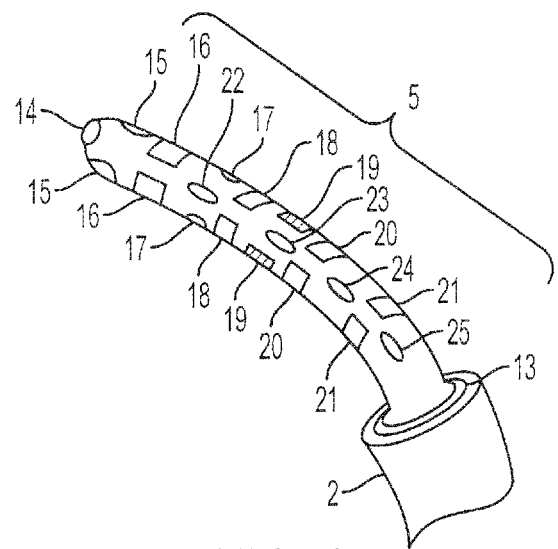
FIGS. 3(A)-(C) are schematic illustrations of details of the catheter's distal tip, as well as schematic diagrams of the electrothermal functionality and mechanical steering capabilities.
Figure 3B:
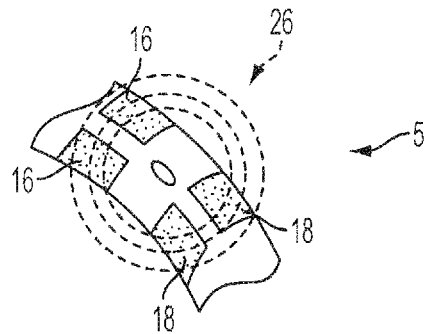
Figure 3C:
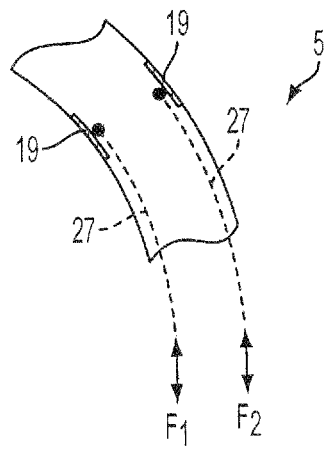

FIG. 3(A) shows the details of construction of the distal end or tip 5. Included in its design are the end port hole 14 through which the irrigation fluid is pumped. The side port holes 15 can be used to augment the irrigation in some embodiments, or as suction ports to remove fluid in other embodiments. The electrodes may include the distal cathodes and anodes 16, 18 respectively, and the proximal cathodes and anodes 20, 21 respectively. Temperature sensors 17 are located on the distal tip. The port holes 22, 23, 24 can be used for additional irrigation, and the port hole 25 can be used for suction. The axial locations of the contact points 19 for the tensioning means used to steer the distal tip may be positioned between the distal anode 18 and the proximal cathode 20. The distal tip 5 extends through the aperture 13 in the distal end of the sheath 2. FIG. 3(B) shows one example of how the electric field lines 26 might emanate between pairs of anodes 18 and cathodes 16. When in contact with the epicardial surface, the resulting current flows give rise to intense localized heating that results in ablation of the targeted epicardial tissues. FIG. 3(C) shows the details of the distal tensioning apparatus. The contact points 19 serve as the distal anchors for the tensioning means 27 which extend along the axial length of the catheter. The tensioning forces, $F_1$ and $F_2$, are adjusted via one of the controls on the handle 6 as per FIG. 1.

It should be appreciated that the medium to flow through ablation catheter device or system may be at least one of the following: agent, substance, material, thrombolytic agents, clot lysis agents, chemotherapies, cell slurries, gene therapy vectors, growth factors, contrast agents, angiogenesis factors, radionuclide slurries, anti-infection agents, anti-tumor compounds, receptor-bound agents and/or other types of drugs, therapeutic agent and/or diagnostic agent, or any combination thereof.

It should be appreciated that any of the components or modules referred to with regards to any of the present invention embodiments discussed herein, may be integrally or separately formed with one another. Further, redundant functions or structures of the components or modules may be implemented. Moreover, the various components may be communicated locally and/or remotely with any user/clinician/patient or machine/system/computer/processor. Moreover, the various components may be in communication via wireless and/or hardwire or other desirable and available communication means, systems and hardware.

Moreover, it should be appreciated that any of the components or modules referred to with regards to any of the present invention embodiments discussed herein, may be a variety of materials and/or composites as necessary or required. Still further, it should be appreciated that any of the components or modules (or combination thereof) may provide shape, size and volume contoured by adjusting its geometry and flexibility/rigidity according to the target location or anatomy (or region, including structure and morphology of any location) being treated.

Figure 4A:
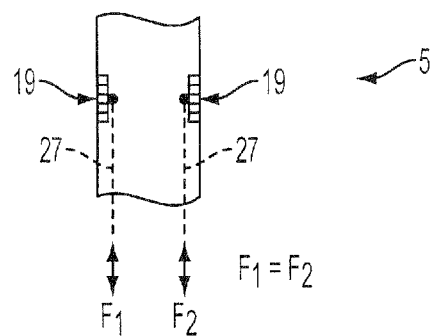
FIGS. 4(A)-(C) are schematic illustrations of the details of the mechanism of action for obtaining bi-directional steering of the distal tip via tensioning means whereby the tip or end is straight, towards the left, and towards the right, respectively.
Figure 4B:
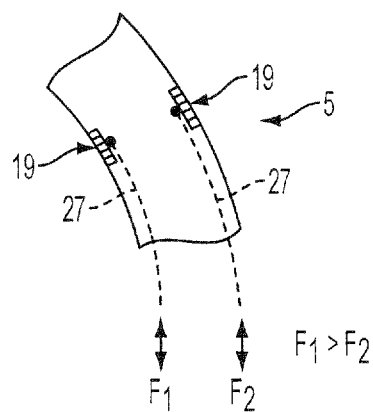
Figure 4C:
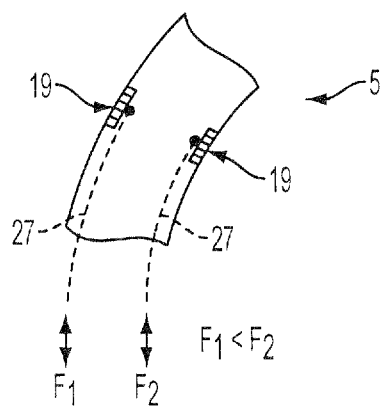
Figure 5A:
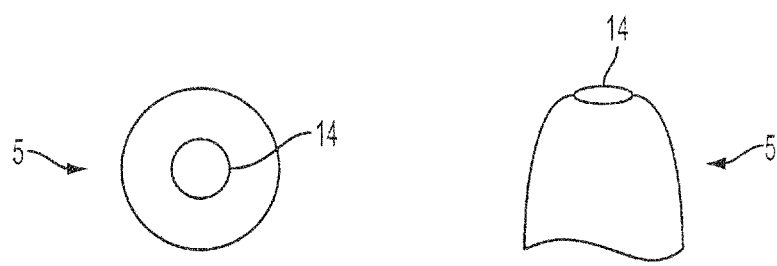
FIGS. 5(A)-(D) are schematic illustrations of exemplary embodiments of configurations of the port holes located at the distal tip.
Figure 5B:
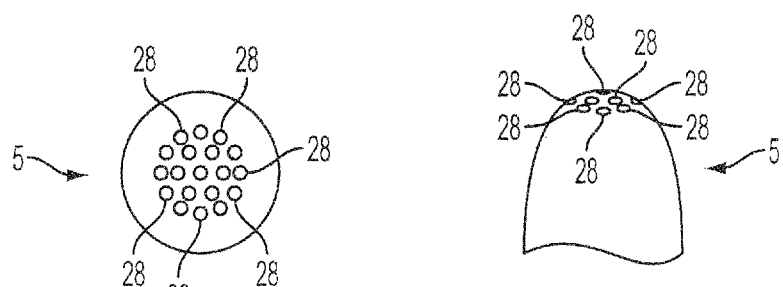
Figure 5C:
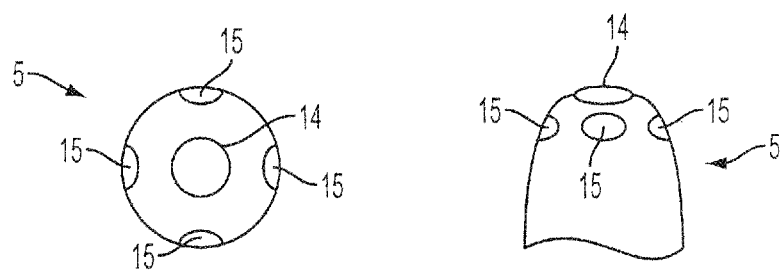
Figure 5D:
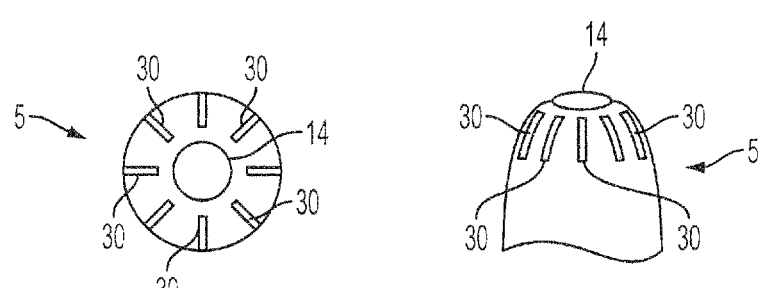

FIG. 4(A) shows that the distal tip or end 5 remains straight when the tensioning means 27 are adjusted such that $F_1=F_2$. When $F_1>F_2$, as in FIG. 4(B), the distal tip or end 5 will be oriented towards the left, and when $F_1<F_2$, as in FIG. 4(C), the distal tip will be oriented towards the right.

It should be appreciated that coaxial alignment or concentric alignment does not need to be exact, but rather one conduit, lumen, sheath, or guidewire slid outside or inside of another.

FIG. 5 shows several different embodiments of the port holes at the end of the distal tip or end 5. For instance, a single circular end-port hole 14 is shown in FIG. 5(A), a plurality of small port holes 28 is shown in FIG. 5(B), an end-port hole 14 and a configuration of distal side-port holes 15 is shown in FIG. 5(C), and an end-port hole 14 and a configuration of radial slits 30 is shown in FIG. 5(D). A variety of aperture alignments and contours may be implemented as desired or required for the medical procedure or anatomy.

Figure 6A:
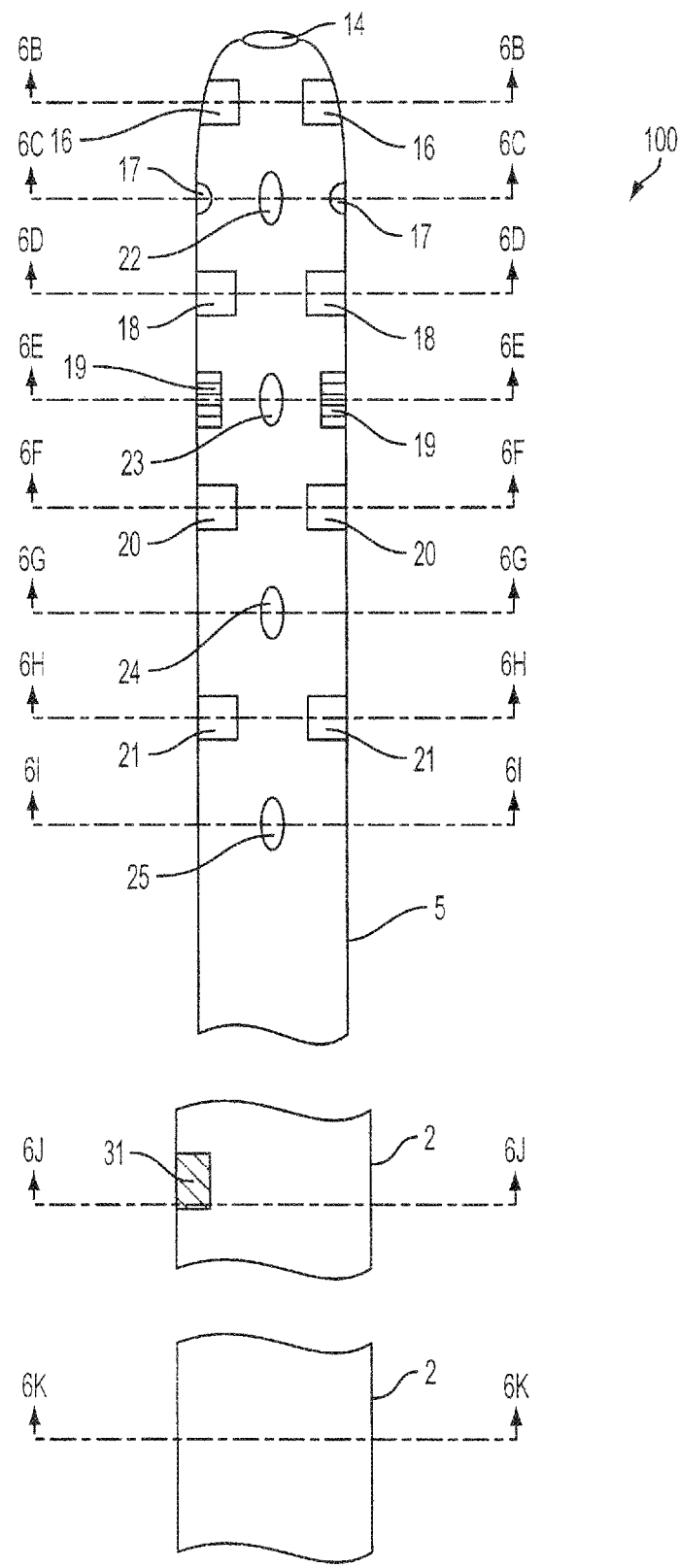
FIG. 6(A) is a schematic illustration of an exemplary ablation catheter.
Figure 6B:
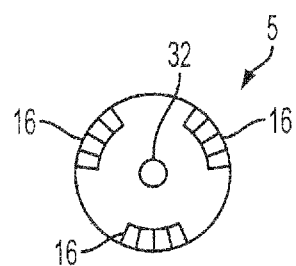
FIGS. 6(B)-6(K) are schematic cross sections of internal structures within the distal tip, axial lumen, and proximal end of the ablation catheter shown in FIG. 6(A).
Figure 6C:
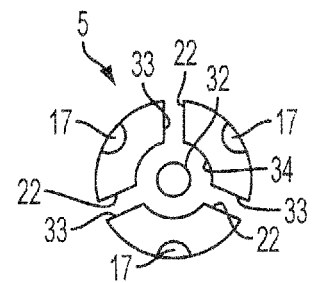
Figure 6D:
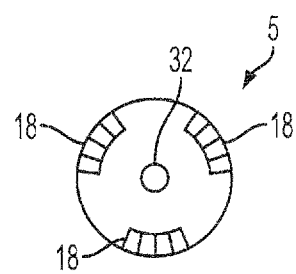
Figure 6E:
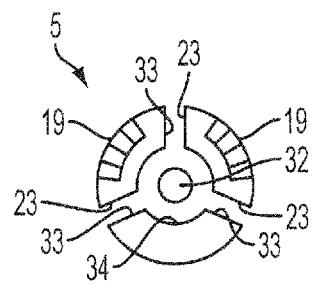
Figure 6F:
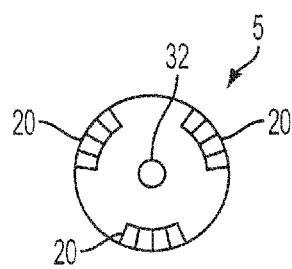
Figure 6G:
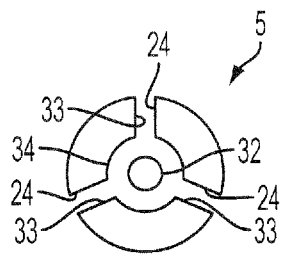
Figure 6H:
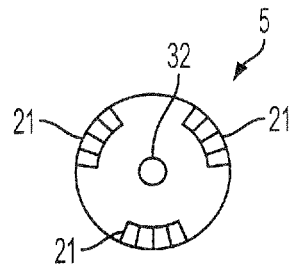
Figure 6I:
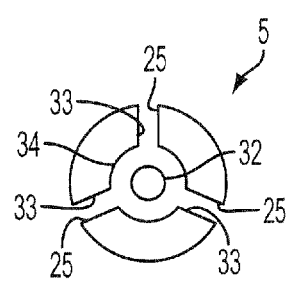
Figure 6J:
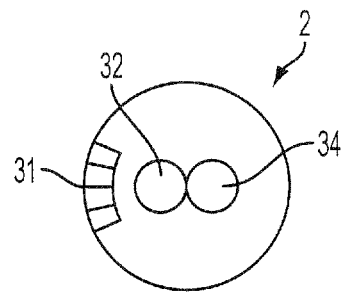
Figure 6K:
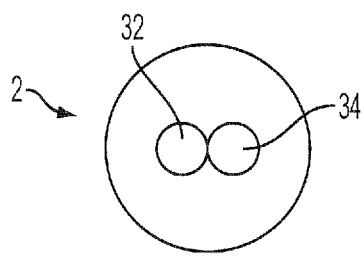

FIGS. 6(A)-6(K) show the cross sectional views (FIGS. 6(B)-6(K)) of the interior of the lumen at different points along the length of the catheter 100 (FIG. 6(A)) preceding an end port hole 14 at the distal tip: at the level of the distal cathode 16 (FIG. 6(B)); at the level of the temperature sensors 17 (FIG. 6(C)); at the level of the distal anode 18 (FIG. 6(D)); at the level of the distal tensioning means contact points 19 (FIG. 6(E)); at the level of the proximal cathode 20 (FIG. 6(F)); at the level of one of the medial port holes 24 (FIG. 6(G)); at the level of the proximal anode 21 (FIG. 6(H)); at the level of the proximal port holes 25 (suction/withdrawal portholes) (FIG. 6(I)); at the level of the proximal tensioning means contact point, 31 (FIG. 6(J)); and within the medial length of the catheter 2 (FIG. 6(K)). The fluid-handling structures within the catheter are the irrigation delivery tube 32 (shown in FIGS. 6(B)-6(K); the connector tubes 33 (for either suction or irrigation, as needed) that couple the delivery tubes 32 (e.g., for irrigation), 34 to the port holes 22, 23, 24; and deliver tube 34 (e.g., for suction) (e.g. as shown in FIGS. 6(C), 6(E), 6(G), and 6(I)-6(K)). A variety of structure/component alignment and location may be implemented as desired or required for the medical procedure or anatomy.

Figure 7A:
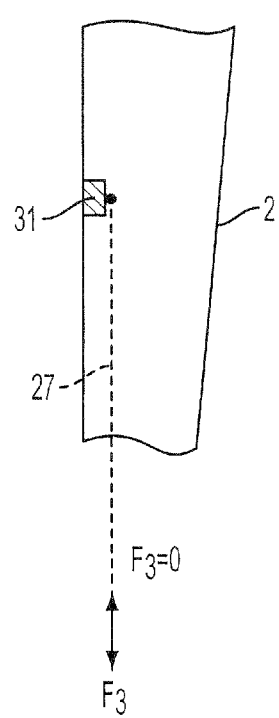
FIGS. 7(A)-(B) are schematic illustrations of the details of an exemplary mechanism of action for directional steering of the medial segment of the device.
Figure 7B:
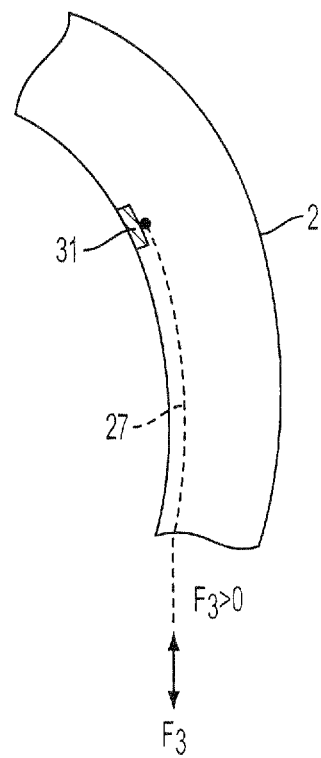

FIG. 7 shows the details of the tensioning mechanism that is used to control the curvature of the sheath 2 at the proximal center of curvature. The tensioning means 27 is attached at a contact point 31 along the axial length of the sheath 2 (or catheter). If the tensioning force $F_3=0$, as shown in FIG. 7(A), then there is no curvature about the proximal point of curvature. However, if $F_3>0$, then the sheath 2 (or catheter) will arc about the proximal point of curvature as shown in FIG. 7(B).

It should be appreciated that the various steering, propulsion, and tensioning means may be applied to the various sheaths, catheters and guidewires, or any related components disclosed herein.

It should be appreciated that the various sheaths, catheters and guidewires, or any related components disclosed herein, may have a circular or oval shaped cross-section or various combinations thereof. Further, it should be appreciated that various sheaths, catheters and guidewires, or any related components disclosed herein may have any variety of cross sections as desired or required for the medical procedure or anatomy.

Figure 8:
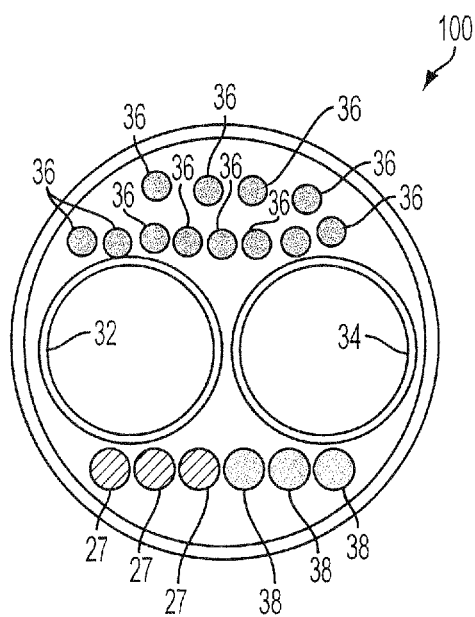
FIG. 8 is a schematic cross sectional view of an embodiment of the arrangement of the elements inside the catheter near its proximal end.

FIG. 8 shows a cross-sectional view of the inner lumen of the catheter 100 which reveals the delivery tubes 32, 34; the three tensioning leads 27; the three temperature sensor leads 38; and the 12 electrical leads 36 one each for the three proximal anodes, the three proximal cathodes, the three distal anodes, and the three distal cathodes.

Figure 9:
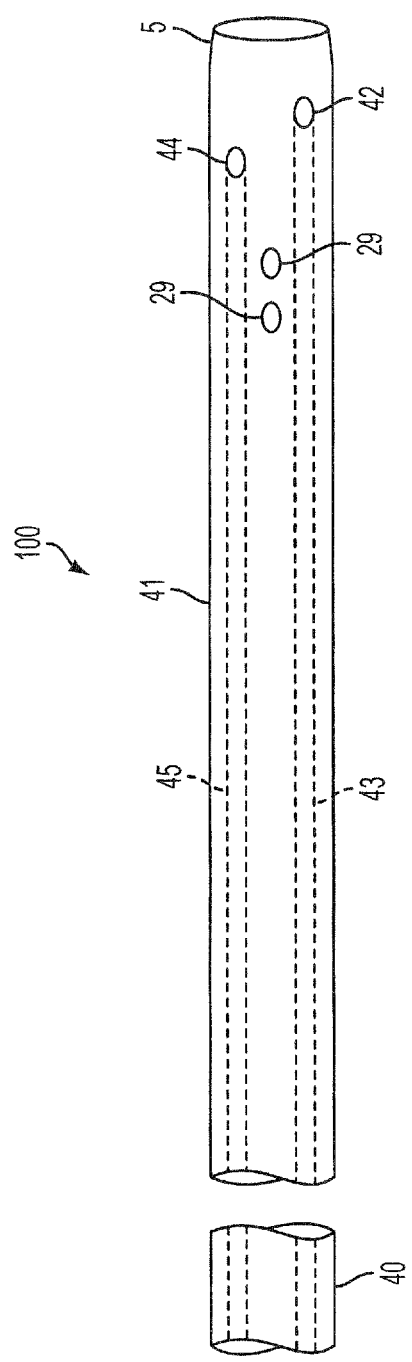
FIG. 9 is a schematic elevation view of an embodiment of the catheter system.

FIG. 9 shows an embodiment of the ablation catheter system with an ablation catheter 100 containing a distal end 5, a proximal end 40, and a longitudinal wall 41 there between. Electrodes 29 in communication with the ablation catheter are present. Also present is a distal irrigation aperture 42 at the distal end 5 in communication with an irrigation lumen 43 extending longitudinally towards the proximal end 40. A distal suction aperture 44 is in communication with a suction lumen 45 extending longitudinally towards the proximal end 40. It should be appreciated that the lumens and apertures may terminate along the longitudinal wall 41 or distal end wall (if any) or proximal end wall (if any, not shown).

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

EXAMPLES

Practice of the invention will be still more fully understood from the following examples, which are presented herein for illustration only and should not be construed as limiting the invention in any way.

Example No. 1

Summary of Dual-Deflectable Irrigated/Suction-Tip Ablation Catheter is provided below.

Some non-limiting exemplary design features of the ablation catheter are:

(1) A length of 90 cm, with an 8 Fr diameter.

(2) Two separate deflectable points. At rest the catheter will be straight. However the distal tip can be deflected through 120 degrees in two directions, approximately 17 mm from the tip. A second deflectable curve will be centered approximately 50 mm proximal to the tip and will be able to deflect through 120 degrees in one direction. The nominal 50 mm length could be variable to create a family of catheters, so that shorter curves would be used in small children while longer curves would be used in larger adults.

(3) Irrigation on the entire end of the catheter with suction at three points just proximal to the second set of electrodes so all sides of the catheter tip are kept cool but the irrigation fluid is sucked back. In addition there will be a backup suction area 20 mm proximal to the catheter tip. The suction lumen will be larger than the irrigation lumen in order to insure good suction and to optimize fluid removal.

(4) A tip split into 3 electrode-bearing segments (labeled A, B, C) each covering 110 degrees in circumference, with 10 degrees of non-electrode area between each segment.

(5) A 2 mm tip instead of the standard 4-8 mm tip.

At the most distal end of the device (i.e., the part farthest from the operator) will be the irrigation port with the three 2 mm ablation tip-anodes each covering 110 degrees of circumference. Five mm proximal to the end will be three 2 mm cathodes to be used with the anodes to record signals or pace tissue prior to ablation. Thus, prior to ablation, the operator could see if the best cardiac signal is on, e.g., the "A" pair or "B" pair. Then, to make sure the phrenic nerve is not in the way, the operator could try to capture the phrenic nerve signal with the "A" pair. If the best cardiac signal is on "A" and the phrenic nerve signal cannot be captured on "A" he could then ablate on "A."

Moving further down from the tip are the suction ports connected to a second inner lumen. Next, 5 mm and 10 mm from the distal end, would be another pair of electrodes (the proximal anode and cathode). Just beyond this point would be the first center of deflection (approximately 12 mm from the distal end).

A second backup set of suction ports is positioned 40 mm from the distal end. These ports are connected to the central lumen. At 50 mm from the distal end would be the other uni-directional center of deflection. At the handle there would be two levers to control the distal and proximal curves via pull wires or some other appropriate tensioning means. Also, associated with the handle means, there would be two ports, one for suction and one for infusion of fluid. In an embodiment, each port would consist of a channel in a three-way stop cock, thus allowing easy clinical access for manual infusion or suction.

In this embodiment, the interior of the catheter would contain lumens for suction and infusion, 8 wires to connect to the 8 electrodes (three on the tip, three of them 4 mm from the tip, one 10 mm from the tip, and one 15 mm from the tip), 3 pull wires to steer the catheter, and any insulation needed for these parts. In another embodiment, the proximal anode and cathode would also consist of three circumferential pairs, thus requiring 12 wires to connect the 12 electrodes.

Example No. 2

In one embodiment, the conductor resistance for anodes and cathodes would be 0.9 Ohms (static). Irrigation would take place at 4 PSI, and suction at 3 PSI. The ablation system would provide electromagnetic shielding, with room for guidance means and/or propulsion means. The ablation catheter would be stiff enough for use in a robotic system, such as the Hansen Sensei system, with a 6.5 Fr outer size and a length of 55 cm. Various robotic systems would provide a means for navigating the ablation catheter and related components disclosed herein.

Example No. 3

Summary of an exemplary Guiding Sheath is provided below.

As explained above conventional guiding sheaths designed for endocardial use have limitations in the endocardium. In particular, conventional endocardial sheaths are long, may have only a single steerable curve (most have no steerable curves) and generally have no ability to suck fluid out once a catheter is inserted.

An embodiment of the present invention pertaining to an epicardial sheath may have, but is not limited thereto, the following characteristics:

(1) A nominal length of 50 cm. Shorter and longer sheaths can be made to create a family of sheaths depending on how much adipose tissue the patient has.

(2) Two separate deflectable points; one bidirectional 20 mm from the end, the other unidirectional 70 mm from the end.

(3) The inner lumen will be of a size that is 2 Fr larger than the ablation catheter to allow suction around the catheter in order to drain any effusions or extra fluid from the irrigated tip, thus creating a third backup suction system.

(4) A variation in the design would have an inner lumen of 8 Fr but have an additional outer lumen for suction.

Example No. 4

An exemplary description of an embodiment incorporating these features would be as follows. A feature of the subject invention is that the sheath has a large (wide) radius of curvature and incorporates two arcs, i.e., has two points of steering. The sheath should be a total 50 cm in length. The sheath should have a 10 Fr (3.3 mm) inner lumen so it can accommodate standard 8 Fr (2.7 mm) ablation catheters and still have enough internal space left to withdraw fluid or retain a guide wire. Outside the inner lumen will be three different tensioning means or pull wires oriented at 0, 90 and 270 degrees around the circumference. The zero-degree (top) wire should extend a length of 10 cm from the proximal end and be used to curve the sheath around the apex of the heart. The other two tensioning means or pull wires (at 90 and 270 degrees) will extend 29 cm from the proximal end (i.e., terminate 1 cm from the distal end) and would be used to bidirectionally steer the sheath at the tip, through angles of up to 90 degrees relative to the uncurved axis of the sheath. Unlike endocardial ablations, there is no need here for a greater-than-90-degree turn. In fact, turns through angles greater than 90 degrees may be clinically dangerous. In the most general version of this sheath, there should be an outer lumen to allow for suction of fluid, unlike the endocardial designs. In an embodiment, the distal tip of the sheath would incorporate a single large torroidal (donut-like) end port hole, as well as a plurality of staggered side port holes all leading to the inside of the outer lumen, so that irrigation fluid and other effluents could be pumped into and sucked out of the pericardium. One purpose of incorporating a plurality of such port holes is to maximize the reliability of fluid withdrawal by minimizing the risk of the simultaneous clogging of a smaller number of port holes. As mentioned above, a variation of the sheath would add an outer lumen. The inner lumen should be connected to an infusion port via a 3-way stopcock at the proximal end of the sheath to allow either for flushing or for the infusion of fluid or of a drug. The outer lumen should also be attached to an infusion port having a 3-way stopcock to enable suction-based removal of fluid. The terminal component at the proximal end of the sheath should incorporate a diaphragm element, as is done in existing sheaths, to allow for the introduction of an ablation catheter.

Example No. 5

Figure 10:
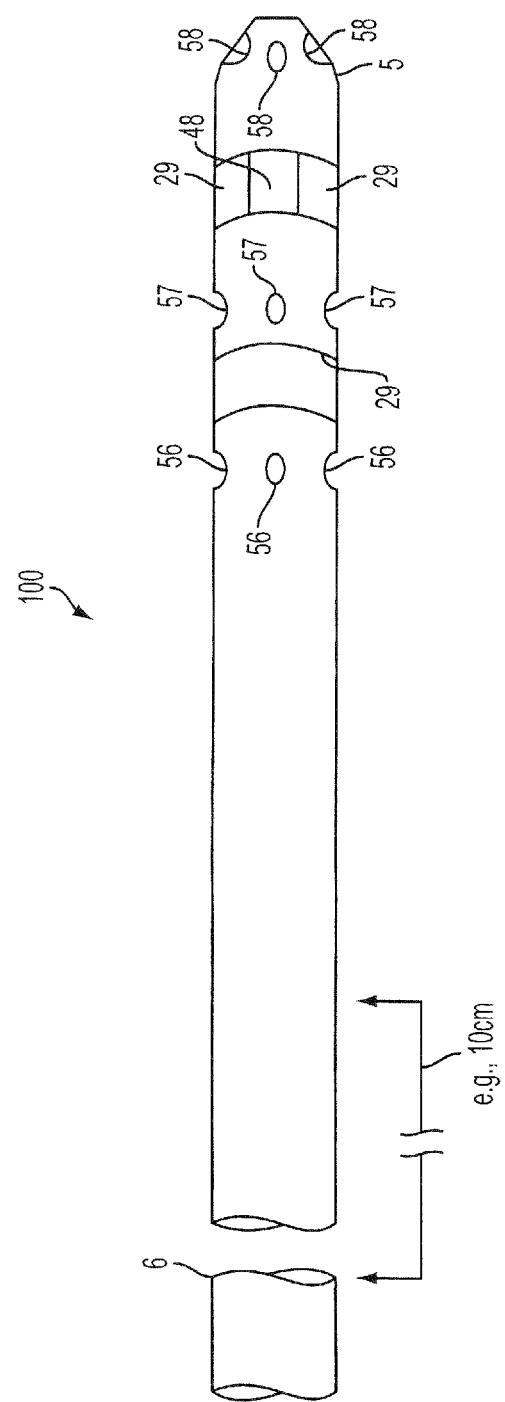
FIG. 10 is a schematic elevation view of an embodiment of the catheter system.

FIG. 10 shows an external elevation view of an embodiment of the ablation catheter system. On the ablation catheter 100 there comprises backup drains 56, proximal electrode 29, suction drains 57, distal electrode 29, insulation 48, and end hole 58 at the distal end 5

Figure 11:
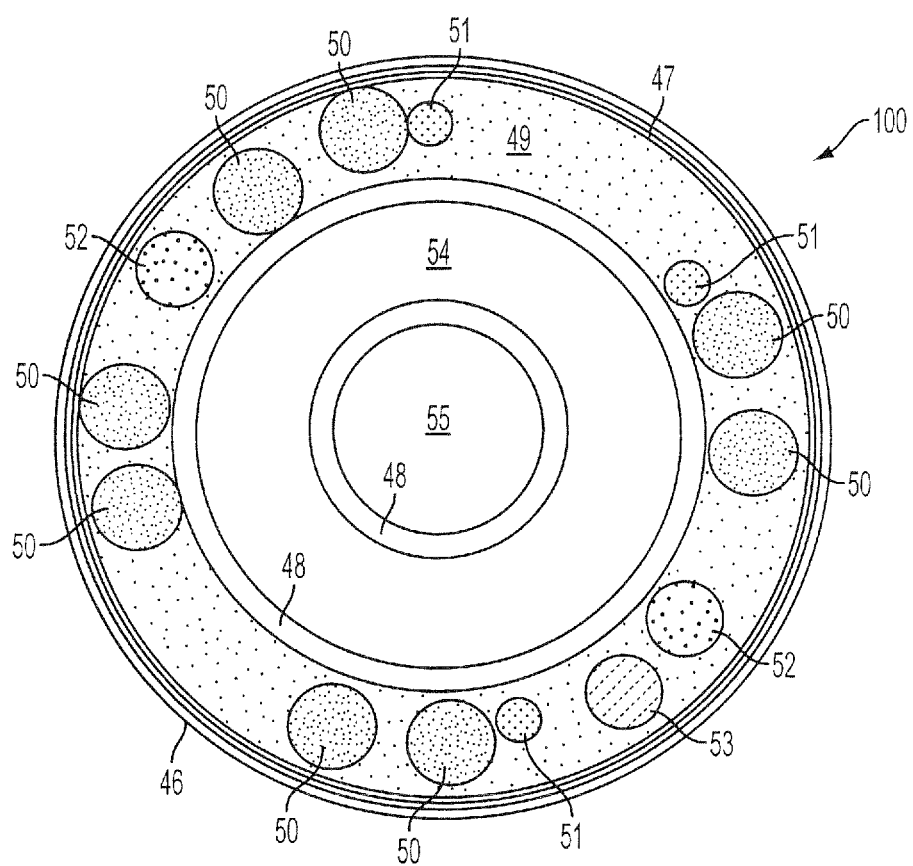
FIG. 11 is a schematic cross sectional view of the catheter of FIG. 10 taken at 10 cm (or other applicable distance as shall be determined) from the handle.

FIG. 11 shows a cross-section of an embodiment of the ablation catheter system 10 cm from the handle 6. It should be appreciated that the length may vary as desired or required as per the medical procedure or anatomy. The ablation catheter 100 contains an outer Teflon-coated silicone layer 46 over a layer of metal/copper shielding 47. Between the metal/copper shielding and a layer of soft silicone insulation 48 is a layer of silicone fill 49. Within the silicone fill 49 layer exists wires 50 that connect to a plurality of distal electrodes. Also within the silicone fill 49 layer is thermocouple wiring 51, distal pull wires 52, and a proximal pull wire 53. Within the silicone fill 49 layer is another layer of soft silicone insulation 48. Beyond this exists an outward channel 54 and an inward channel 55 separated by yet another layer of silicone insulation 48. These channels could be used to deliver and extract saline solution, for example, or other fluid or medium as desired or required.

Figure 12:
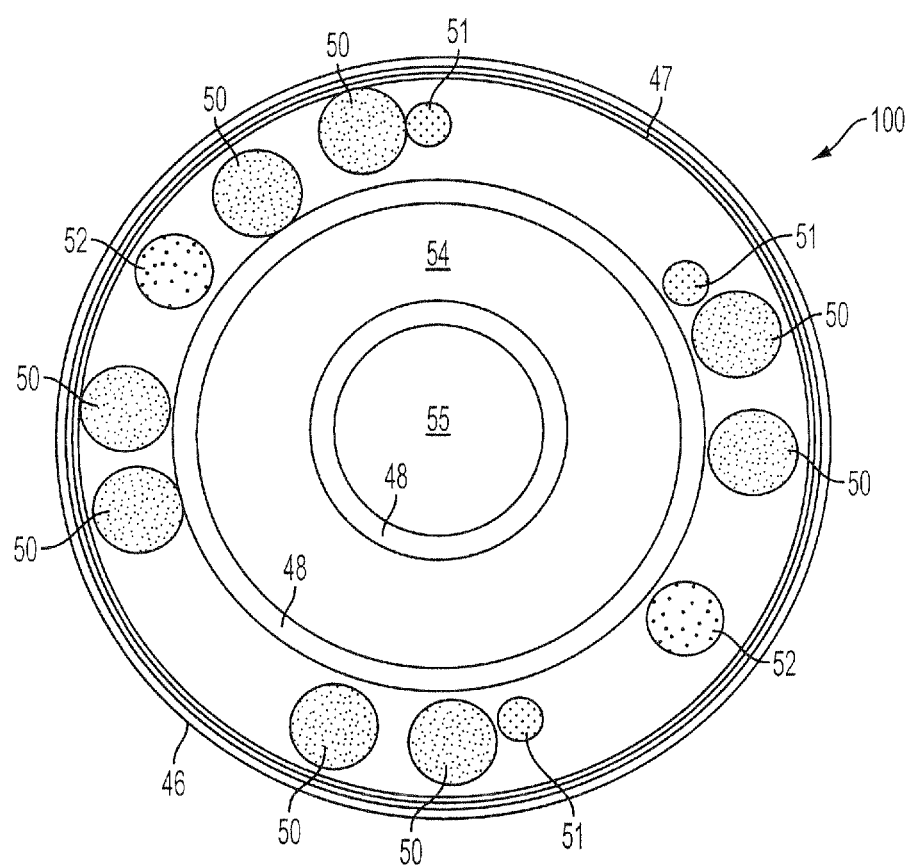
FIG. 12 is a schematic cross sectional view of the catheter of FIG. 10 taken at 15 cm (or other applicable distance as shall be determined) from the handle.

FIG. 12 shows a cross-section of an embodiment of the ablation catheter system 15 cm from the handle 6. It should be appreciated that the length may vary as desired or required as per the medical procedure or anatomy. The ablation catheter 100 contains an outer Teflon-coated silicone layer 46 over a layer of metal/copper shielding 47. Between the metal/copper shielding 47 and a layer of soft silicone insulation 48 there exists electrode wiring 50 to six distal electrodes. Each of the three pairs of wires are oriented at 120 degrees. Also present are thermocouple wiring 51 and distal pull wires 52. Within this region exists soft silicone insulation 48. Beyond this exists an outward channel 54 and an inward channel 55 separated by yet another layer of silicone insulation 48. These channels could be used to deliver and extract saline solution, for example, or other fluid or medium as desired or required.

Figure 13:
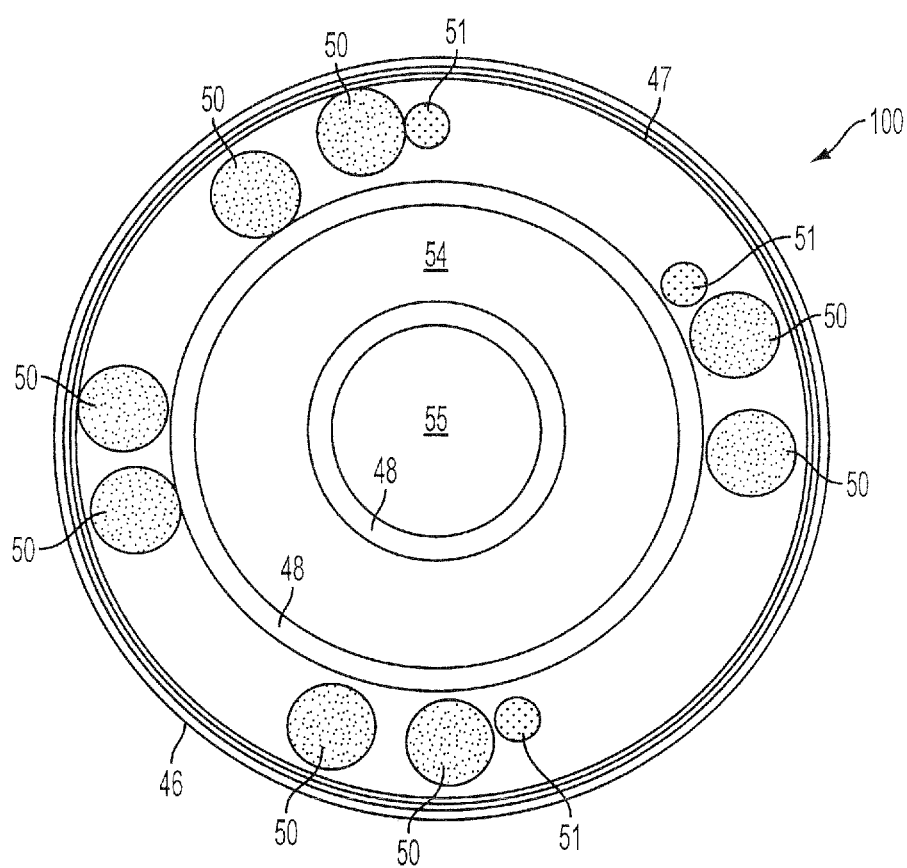
FIG. 13 is a schematic cross sectional view of the catheter of FIG. 10 taken at 52 cm (or other applicable distance as shall be determined) from the handle.

FIG. 13 shows a cross-section of an embodiment of the ablation catheter system 52 cm from the handle 6 after distal steering. It should be appreciated that the length may vary as desired or required as per the medical procedure or anatomy. The ablation catheter 100 contains an outer Teflon-coated silicone layer 46 over a layer of metal/copper shielding 47. Between the metal/copper shielding and a layer of soft silicone insulation 48 exists electrode wiring 50 to six distal electrodes. Each of the three pairs of wires are oriented at 120 degrees. Also present is thermocouple wiring 51. Within this region exists soft silicone insulation 48. Beyond this exists an outward channel 54 and an inward channel 55 separated by yet another layer of silicone insulation 48. These channels could be used to deliver and extract saline solution, for example, or other fluid or medium as desired or required.

Figure 14:
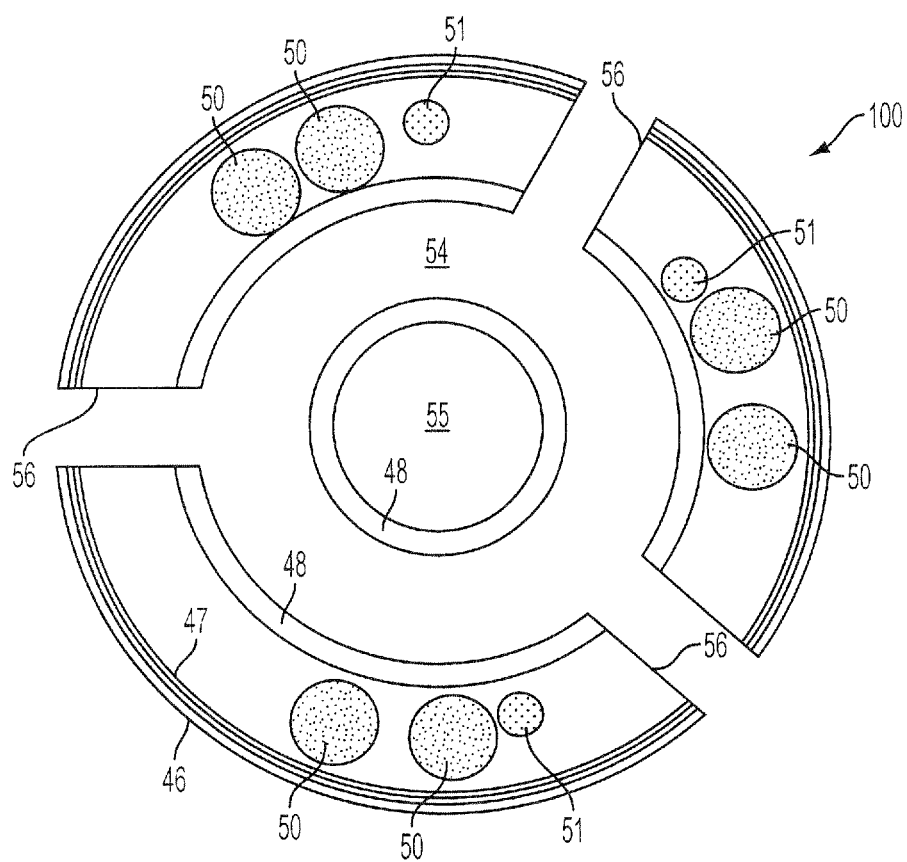
FIG. 14 is a schematic cross sectional view of the catheter of FIG. 10 taken at 52.5 cm (or other applicable distance as shall be determined) from the handle.

FIG. 14 shows a cross-section of an embodiment of the ablation catheter system 52.5 cm from the handle 6. It should be appreciated that the length may vary as desired or required as per the medical procedure or anatomy. The ablation catheter 100 contains an outer Teflon-coated silicone layer 46 over a layer of metal/copper shielding 47. Between the metal/copper shielding and a layer of soft silicone insulation 48 exists electrode wiring 50 to six distal electrodes. Each of the three pairs of wires are oriented at 120 degrees. Also present is thermocouple wiring 51. Within this region is another layer of soft silicone insulation 48. Beyond this exists an outward channel 54 and an inward channel 55 separated by yet another layer of silicone insulation 48. These channels could be used to deliver and extract saline solution, for example, or other fluid or medium as desired or required. Backup drains 56 are oriented radially outward at about 120 degrees, providing a means of egress from the outward channel 54. These backup drains are offset from the primary drains in cases attached to the heart.

Figure 15:
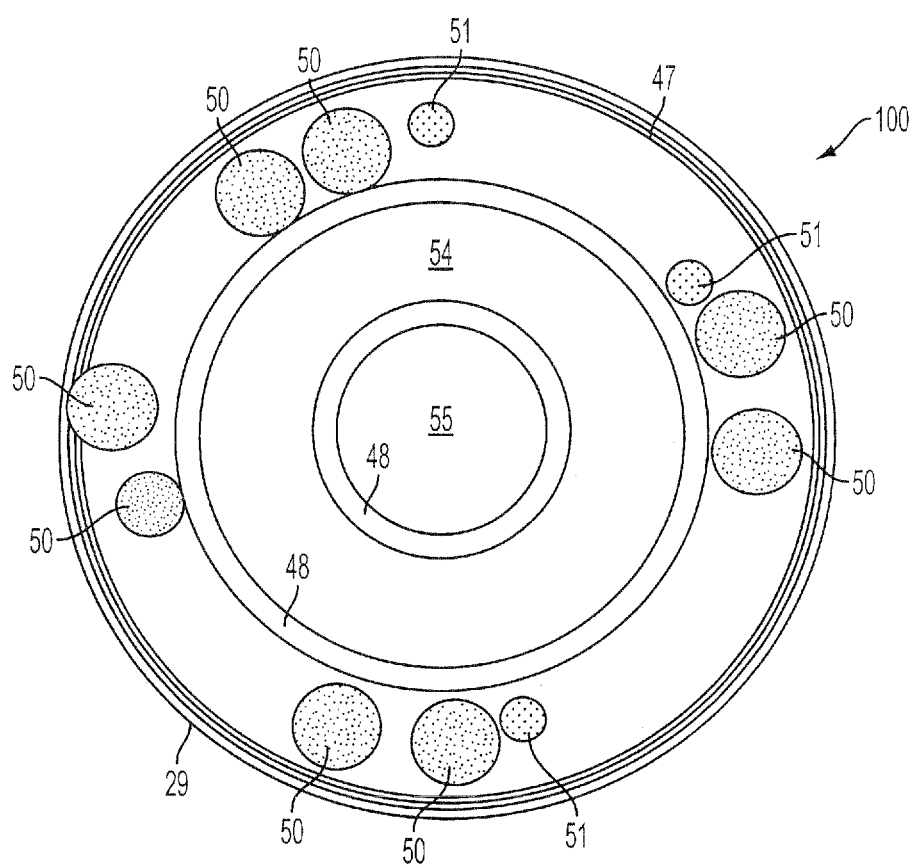
FIG. 15 is a schematic cross sectional view of the catheter of FIG. 10 taken at 53 cm (or other applicable distance as shall be determined) from the handle.

FIG. 15 shows a cross-section of an embodiment of the ablation catheter system 53 cm from the handle 6. It should be appreciated that the length may vary as desired or required as per the medical procedure or anatomy. The ablation catheter 100 contains an outer electrode 29. Within the layer below the electrode 29 exists electrode wiring 50 to six distal electrodes. Each of the three pairs of wires are oriented at 120 degrees. Also within this region is thermocouple wiring 51. Within this region is another layer of soft silicone insulation 48. Beyond this exists an outward channel 54 and an inward channel 55 separated by yet another layer of silicone insulation 48. These channels could be used to deliver and extract saline solution, for example.

Figure 16:
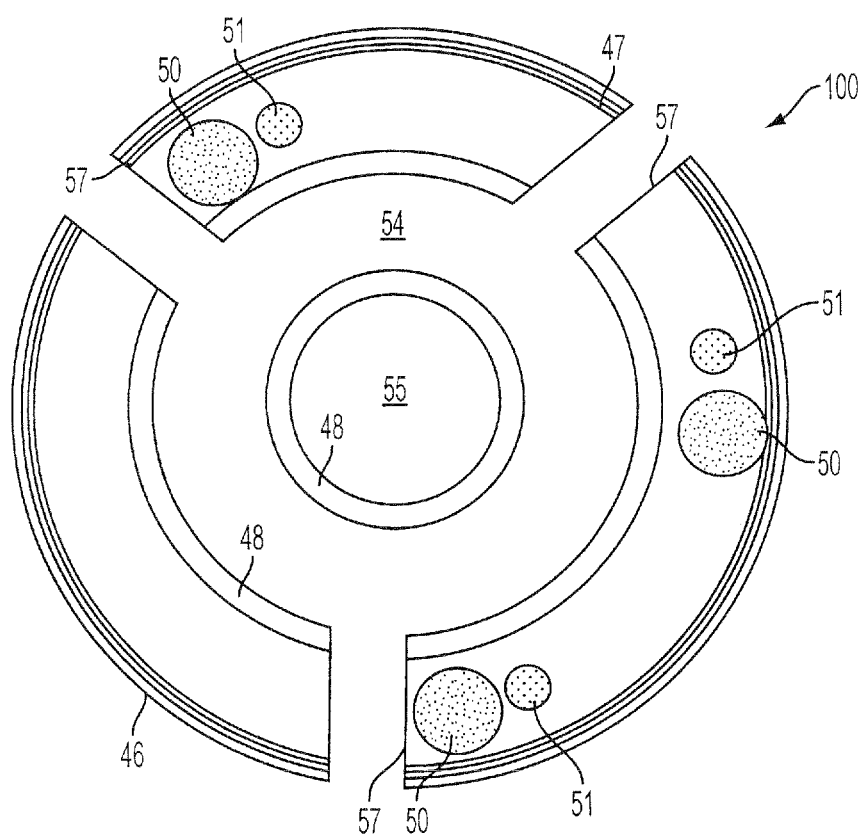
FIG. 16 is a schematic cross sectional view of the catheter of FIG. 10 taken at 53.5 cm (or other applicable distance as shall be determined) from the handle.

FIG. 16 shows a cross-section of an embodiment of the ablation catheter system 53.5 cm from the handle 6. It should be appreciated that the length may vary as desired or required as per the medical procedure or anatomy. The ablation catheter 100 contains an outer Teflon-coated silicone layer 46 over a layer of metal/copper shielding 47. Between the metal/copper shielding and a layer of soft silicone insulation 48 exists electrode wiring 50 to distal electrodes. Each of the three wires are oriented at 120 degrees. Also within this region is thermocouple wiring 51. Within this region is another layer of soft silicone insulation 48. Beyond this exists an outward channel 54 and an inward channel 55 separated by yet another layer of silicone insulation 48. These channels could be used to deliver and extract saline solution, for example. Suction drains 57 are oriented radially outward at 120 degrees, providing a means of egress from the outward channel 54.

Figure 17:
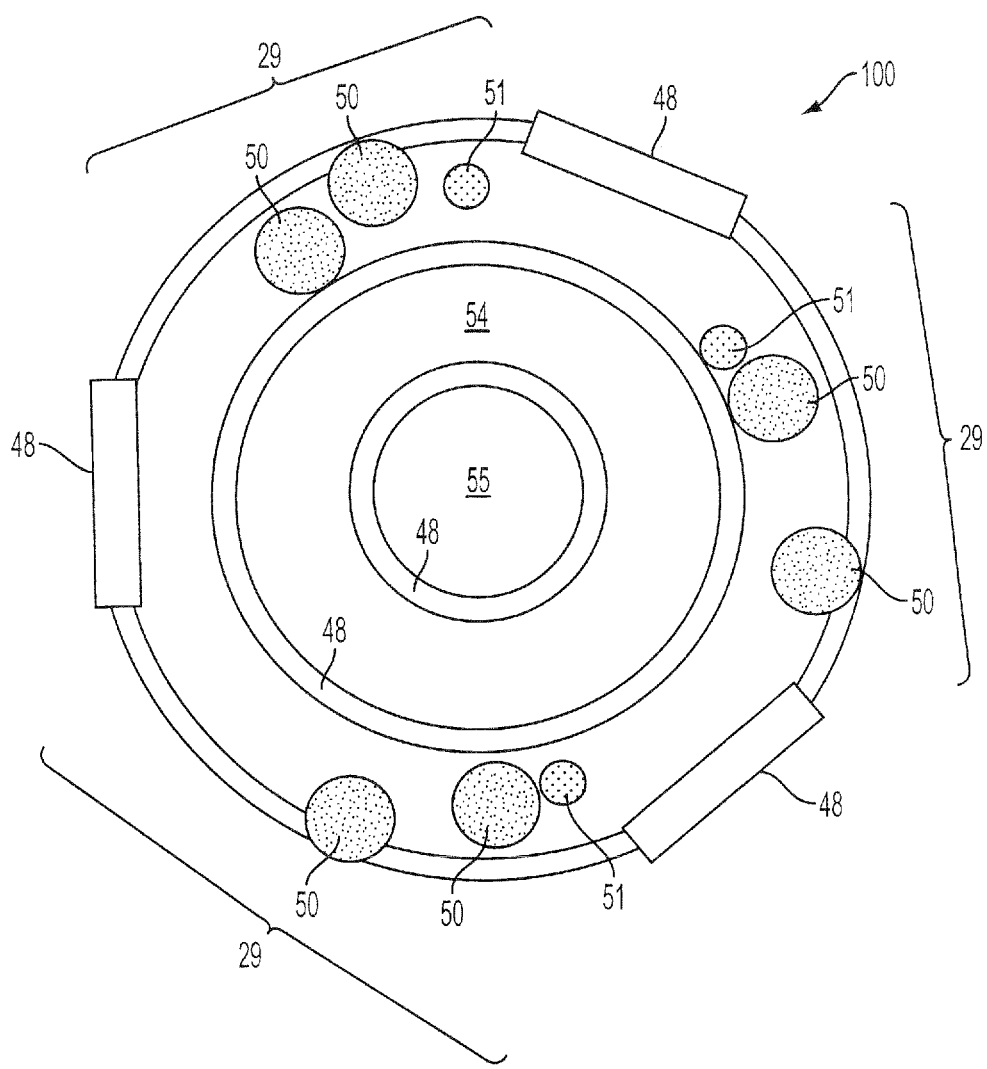
FIG. 17 is a schematic cross sectional view of the catheter of FIG. 10 taken at 54 cm (or other applicable distance as shall be determined) from the handle.

FIG. 17 shows a cross-section of an embodiment of the ablation catheter system 54 cm from the handle 6. It should be appreciated that the length may vary as desired or required as per the medical procedure or anatomy. The ablation catheter 100 contains three separate outer electrodes 29 separated by insulation 48. Within this outer layer exists electrode wiring 50 to six distal electrodes. Each of the three pairs of wires are oriented at 120 degrees. Also within this layer is thermocouple wiring 51. Beyond this layer is another layer of soft silicone insulation 48. Beyond this exists an outward channel 54 and an inward channel 55 separated by yet another layer of silicone insulation 48. These channels could be used to deliver and extract saline solution, for example, or other fluid or medium as desired or required.

Figure 18:
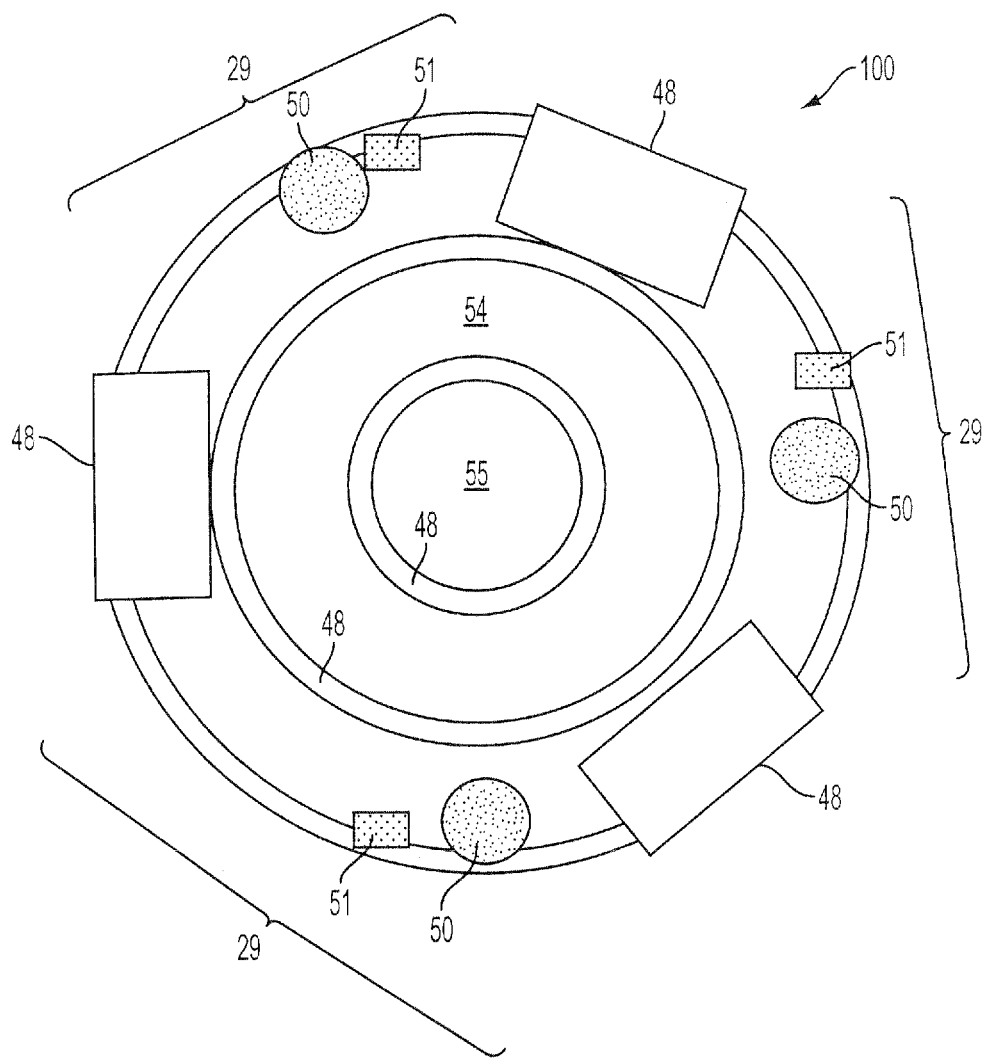
FIG. 18 is a schematic cross sectional view of the catheter of FIG. 10 taken at 54.5 cm (or other applicable distance as shall be determined) from the handle.

FIG. 18 shows a cross-section of an embodiment of the ablation catheter system 54.5 cm from the handle 6. It should be appreciated that the length may vary as desired or required as per the medical procedure or anatomy. The ablation catheter 100 contains three separate outer electrodes 29 separated by insulation 48. Within this outer layer exists electrode wiring 50. Each of the wires are oriented at 120 degrees. Also within this layer is thermocouple wiring 51. Beyond this layer is another layer of soft silicone insulation 48. Beyond this exists an outward channel 54 and an inward channel 55 separated by yet another layer of silicone insulation 48. These channels could be used to deliver and extract saline solution, for example.

Figure 19:
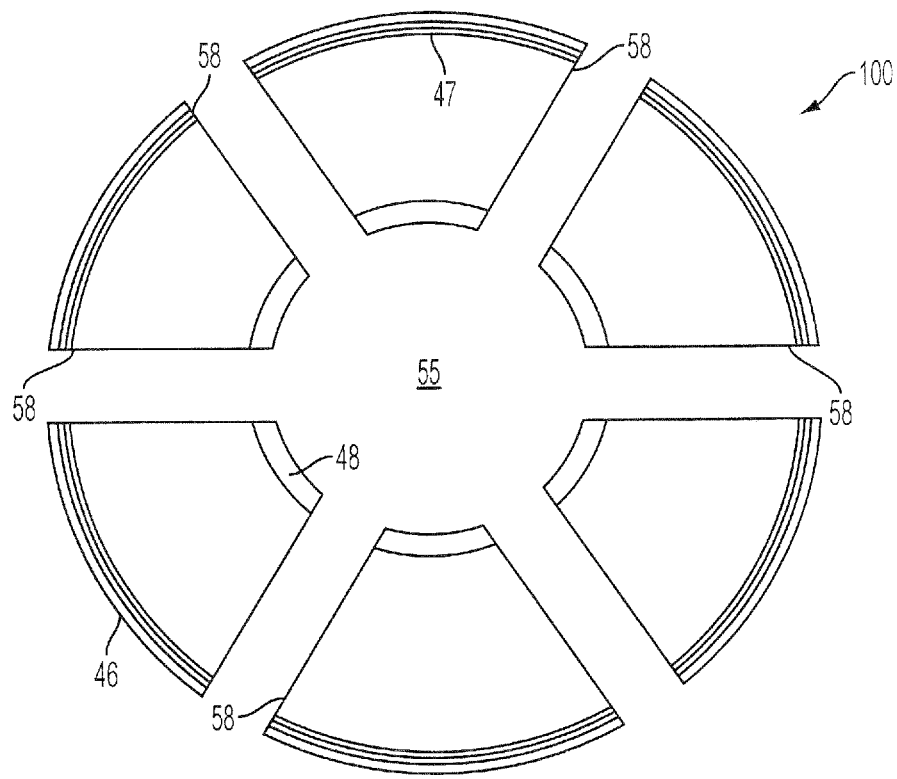
FIG. 19 is a schematic cross sectional view of the catheter of FIG. 10 taken at 55 cm (or other applicable distance as shall be determined) from the handle.

FIG. 19 shows a cross-section of an embodiment of the ablation catheter system 55 cm from the handle 6. It should be appreciated that the length may vary as desired or required as per the medical procedure or anatomy. The ablation catheter 100 contains an outer Teflon-coated silicone layer 46 over a layer of metal/copper shielding 47. Within a layer of silicone insulation 48 exists an inward channel 55. Six end holes 58 extend radially outward from the inward channel 55 providing a means of ingress.

REFERENCES CITED

The following patents, applications and publications as listed below and throughout this document are hereby incorporated by reference in their entirety herein.

The devices, systems, compositions and methods of various embodiments of the invention disclosed herein may utilize aspects disclosed in the following references, applications, publications and patents and which are hereby incorporated by reference herein in their entirety:

| U.S. PATENT AND APPLICATION DOCUMENTS | | | |
|---|---|---|---|
| 7,147,633 | December 2006 | Chee et al | 606/41 |
| 7,146,225 | December 2006 | Guenst et al | 607/119 |
| 7,101,362 | September 2006 | Vanney | 604/523 |
| 7,090,637 | August 2006 | Danitz et al | 600/141 |
| 7,041,099 | May 2006 | Thomas et al | 606/41 |
| 6,974,454 | December 2005 | Hooven | 606/41 |
| 6,960,205 | November 2005 | Jahns et al | 606/41 |
| 6,916,318 | July 2005 | Francischelli et al | 606/41 |
| 6,849,075 | February 2005 | Bertolero et al | 606/41 |
| 6,827,715 | December 2004 | Francischelli et al | 606/34 |
| 6,827,714 | December 2004 | Swanson | 606/32 |
| 6,752,805 | June 2004 | Maguire et al | 606/41 |
| 6,723,092 | April 2004 | Brown et al | 606/41 |
| 6,689,128 | February 2004 | Sliwa et al | 606/41 |
| 6,558,382 | May 2003 | Jahns et al | 606/41 |
| 6,231,518 | May 2001 | Grabek et al | 600/508 |
| 6,206,004 | May 2001 | Schmidt et al | 604/500 |
| 6,156,009 | December 2000 | Grabek | 604/117; |
| 5,972,013 | October 1999 | Schmidt | 606/185 |

U.S. Pat. Application Publication 2002/0045895 A1 to Sliwa et al., Apr. 18, 2002

| FOREIGN PATENT DOCUMENTS | | |
|---|---|---|
| EP | 1181896 | February 2002 |
| WO | 01/05306 | January 2002 |
| WO | 01/80757 | November 2001 |
| WO | 01/68173 | September 2001 |
| WO | 01/58373 | August 2001 |
| WO | 01/80724 | April 2001 |
| WO | 99/18869 | April 1999 |
| Au | 70522/96 | October 1996 |
| WO | 95/10319 | April 1995 |
| DE | 43 13 903 | September 1994 |
| WO | 93/20886 | October 1993 |
| EP | 0 450 608 | October 1991 |
| CA | 2236958 | July 1973 |

OTHER PUBLICATIONS

A. d'Avila et al., "Transthoracic Epicardial Catheter Ablation of Ventricular Tachycardia," Heart Rhythmn, Vol. 3, pp. 1110-1111, (2006).

E. Sosa et al., "Epicardial Mapping and Ablation Techniques to Control Ventricular Tachycardia," Journal of Cardiovascular Electrophysiology, Vol. 16, pp. 449-452, (2005).

S. Mahapatra et al., "Incidence and Predictors of Cardiac Perforation after permanent Pacemaker Placement," Heart Rhythm, Vol. 2, pp. 907-911, (2005).

D. L. Packer et al., "Multimodality 3-D Ultrasound and Computed Tomographic Image Fusion: A Novel Basis for Catheter Navigation and Electroanatomic Mapping," Circulation, Vol. 112, p. U684, (2005).

E. Sosa et al., "Nonsurgical Transthoracic Epicardial Approach in Patients with Ventricular Tachycardia and Previous Cardiac Surgery," Journal of Interventional Cardiac Electrophysiology, Vol. 10, pp. 281-288, (2004).

W. P. Beukema et al., "Radiofrequency Ablation of Atrial Fibrillation in Patients Undergoing Concommitant Cardiac Surgery. First Experience," PACE, Vol. 20 (Part II), p. 1100, (April 1997).

L. S. Klein et al., "Radiofrequency Ablation of Cardiac Arrhythmias," Scientific American Science & Medicine, pp. 48-57, (May/June 1994).

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes which come within the meaning and range of equivalency of the claims are therefore intended to be embraced herein.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary.

Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed is:

1. An ablation catheter system comprising:
   an ablation catheter including a distal end, a proximal end, and a longitudinal wall therebetween;
   a catheter steering mechanism configured to change a geometry of said ablation catheter within a body of a subject;
   a catheter control device configured to manipulate said catheter steering mechanism;
   a plurality of electrodes disposed at said distal end of said ablation catheter;
   a plurality of distal irrigation apertures at said distal end of said ablation catheter, the plurality of irrigation apertures positioned in a row that extends proximally from the tip of the ablation catheter toward the handle, said plurality of distal irrigation apertures in fluid communication with one or more irrigation lumens extending longitudinally toward said proximal end of said ablation catheter;
   one or more distal suction apertures at said distal end of the ablation catheter, said one or more distal suction apertures in fluid communication with one or more suction lumens extending longitudinally toward said proximal end of said ablation catheter;
   a sheath including a distal end, a proximal end, and a longitudinal wall therebetween, said sheath configured to receive said ablation catheter therein; and
   a sheath steering mechanism that is separate and distinct from the catheter steering mechanism and that is configured to change a geometry of said sheath within the body of the subject,
   wherein, said plurality of electrodes include at least one of:
      an anode and a cathode,
      a plurality of electrodes arranged in a circumferential array around said distal end of said ablation catheter, and
      a plurality of electrodes longitudinally separated on said distal end of said ablation catheter, and
      wherein, a total length of said sheath is less than 30 cm.

2. The ablation catheter system of claim 1, wherein:
   said plurality of distal irrigation apertures includes an end port hole disposed at a tip of said ablation catheter;
   said one or more distal suction apertures include a suction port hole spaced apart from said end port hole along a length of said distal end; and
   said plurality of electrodes include an anode and a cathode disposed at different locations between said end porthole and said suction port hole.

3. The ablation catheter system of claim 2, further comprising a temperature sensor on the distal end of the ablation catheter disposed at a location between said anode and said cathode.

4. The ablation catheter system of claim 1, wherein said longitudinal wall of said ablation catheter includes a plurality of pre-formed curves at different locations along a length of said longitudinal wall.

5. The ablation catheter system of claim 1, wherein said ablation catheter comprises a preconfigured distal center of curvature and a preconfigured proximal center of curvature.

6. The ablation catheter system of claim 5, wherein said catheter steering mechanism further comprises:
   a catheter distal steering mechanism configured to change a geometry of said ablation catheter about said preconfigured distal center of curvature, and
   a catheter proximal steering mechanism configured to change a geometry of said ablation catheter about said preconfigured proximal center of curvature.

7. The ablation catheter system of claim 6, wherein said distal steering mechanism attaches to said ablation catheter at said preconfigured distal center of curvature, and said proximal steering mechanism attaches to said ablation catheter at said preconfigured proximal center of curvature.

8. The ablation catheter system of claim 1, wherein said longitudinal wall of said sheath includes a plurality of pre-formed curves at different locations along a length of said longitudinal wall of said sheath.

9. The ablation catheter system of claim 1, wherein said sheath comprises a preconfigured distal center of curvature and a preconfigured proximal center of curvature.

10. The ablation catheter system of claim 9, wherein said sheath steering mechanism further comprises: a sheath distal steering mechanism configured to change a geometry of said sheath about said preconfigured distal center of curvature, and a sheath proximal steering mechanism configured to change a geometry of said sheath about said preconfigured proximal center of curvature.

11. The ablation catheter system of claim 1, wherein:
   said ablation catheter includes a preconfigured distal center of curvature and a preconfigured proximal center of curvature;
   said catheter steering mechanism includes a catheter distal steering mechanism configured to change a geometry of said ablation catheter about said preconfigured distal center of curvature, and a catheter proximal steering mechanism configured to change a geometry of said ablation catheter about said preconfigured proximal center of curvature;
   said sheath includes a preconfigured distal center of curvature and a preconfigured proximal center of curvature; and
   said sheath steering mechanism includes a sheath distal steering mechanism configured to change a geometry of said sheath about said preconfigured distal center of curvature of the sheath, and a sheath proximal steering mechanism configured to change a geometry of said sheath about said preconfigured proximal center of curvature of the sheath.

12. The ablation catheter system of claim 1, wherein said ablation catheter is configured to be disposed in a thorax of the subject.

13. The ablation catheter system of claim 1, further comprising a temperature sensor disposed at said distal end of said ablation catheter.

14. The ablation catheter system of claim 13, wherein said temperature sensor is configured to provide temperature information on temperatures of tissue during ablation.

15. The ablation catheter system of claim 1, wherein said one or more distal suction apertures comprises a plurality of distal suction apertures.

\* \* \* \* \*